US009572983B2

(12) United States Patent
Levine et al.

(10) Patent No.: US 9,572,983 B2
(45) Date of Patent: Feb. 21, 2017

(54) DEVICES AND METHODS FOR MODULATION OF BONE EROSION

(71) Applicant: SetPoint Medical Corporation, Valencia, CA (US)

(72) Inventors: Jacob A. Levine, Queens, NY (US); Michael A. Faltys, Valencia, CA (US); Ralph J. Zitnik, Santa Barbara, CA (US)

(73) Assignee: SetPoint Medical Corporation, Valencia, CA (US)

( * ) Notice: Subject to any disclaimer, the term of this patent is extended or adjusted under 35 U.S.C. 154(b) by 528 days.

(21) Appl. No.: 13/851,013

(22) Filed: Mar. 26, 2013

(65) Prior Publication Data

US 2013/0253413 A1 Sep. 26, 2013

Related U.S. Application Data

(60) Provisional application No. 61/615,777, filed on Mar. 26, 2012.

(51) Int. Cl.
*A61N 1/36* (2006.01)
*A61N 1/32* (2006.01)

(52) U.S. Cl.
CPC ....... *A61N 1/36053* (2013.01); *A61N 1/36175* (2013.01); *A61N 1/326* (2013.01)

(58) Field of Classification Search
CPC . A61N 1/326; A61N 1/36053; A61N 1/36175
See application file for complete search history.

(56) References Cited

U.S. PATENT DOCUMENTS

| 2,164,121 A | 6/1939 | Pescador |
| 3,363,623 A | 1/1968 | Atwell |
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |

(Continued)

FOREIGN PATENT DOCUMENTS

| CN | 201230913 | 5/2009 |
| CN | 101528303 A | 9/2009 |

(Continued)

OTHER PUBLICATIONS

US 6,184,239, 02/2001, Puskas (withdrawn)

(Continued)

*Primary Examiner* — Amanda Patton
(74) *Attorney, Agent, or Firm* — Shay Glenn LLP

(57) ABSTRACT

Devices and methods for stimulation of the vagus nerve to modulate (e.g., reduce, suppress, etc.) bone erosion. Methods and apparatus for modulating bone erosion may modulate levels of Receptor Activator for Nuclear Factor κ B Ligand (RANKL), and/or to modulate (increase, enhance, etc.) osteoprotegerin (OPG) and/or OPG/RANKL ratio. Devices may include electrical stimulation devices that may be implanted, and may be activated to apply current for a proscribed duration, followed by a period without stimulation.

12 Claims, 20 Drawing Sheets

(56) References Cited

U.S. PATENT DOCUMENTS

| | | |
|---|---|---|
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thomspon et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |

(56) References Cited

U.S. PATENT DOCUMENTS

| | | |
|---|---|---|
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,843,210 B2 | 9/2014 | Simon et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0125044 A1 | 6/2005 | Tracey et al. |
| 2005/0131467 A1 | 6/2005 | Boveja |

(56) References Cited

U.S. PATENT DOCUMENTS

| | | |
|---|---|---|
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0282906 A1 | 12/2005 | Tracey et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |

(56) References Cited

U.S. PATENT DOCUMENTS

| | | |
|---|---|---|
| 2008/0021520 A1 | 1/2008 | Dietrich |
| 2008/0046055 A1 | 2/2008 | Durand et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0208266 A1 | 8/2008 | Lesser et al. |
| 2008/0234790 A1 | 9/2008 | Bayer et al. |
| 2008/0249439 A1 | 10/2008 | Tracey et al. |
| 2008/0281365 A1 | 11/2008 | Tweden et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0105782 A1 | 4/2009 | Mickle et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0247934 A1 | 10/2009 | Tracey et al. |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2010/0003656 A1 | 1/2010 | Kilgard et al. |
| 2010/0010603 A1 | 1/2010 | Ben-David et al. |
| 2010/0042186 A1 | 2/2010 | Ben-David et al. |
| 2010/0063563 A1 | 3/2010 | Craig |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2010/0312320 A1 | 12/2010 | Faltys et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0106208 A1 | 5/2011 | Faltys et al. |
| 2011/0144717 A1 | 6/2011 | Burton et al. |
| 2011/0190849 A1 | 8/2011 | Faltys et al. |
| 2011/0307027 A1 | 12/2011 | Sharma et al. |
| 2012/0065706 A1 | 3/2012 | Vallapureddy et al. |
| 2012/0185009 A1 | 7/2012 | Kornet et al. |
| 2012/0290035 A1 | 11/2012 | Levine et al. |
| 2013/0079834 A1 | 3/2013 | Levine |
| 2013/0245718 A1 | 9/2013 | Birkholz et al. |
| 2014/0074186 A1 | 3/2014 | Faltys et al. |
| 2014/0330349 A1 | 11/2014 | Levine et al. |
| 2015/0066123 A1 | 3/2015 | Faltys et al. |
| 2015/0100100 A1 | 4/2015 | Tracey et al. |
| 2016/0038745 A1 | 2/2016 | Faltys et al. |
| 2016/0051813 A1 | 2/2016 | Faltys et al. |
| 2016/0067497 A1 | 3/2016 | Levine et al. |

FOREIGN PATENT DOCUMENTS

| | | |
|---|---|---|
| CN | 101868280 A | 10/2010 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 0/1910 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |

OTHER PUBLICATIONS

Zitnik et al.; U.S. Appl. No. 14/630,613 entitled "Vagus nerve stimulation screening test," filed Feb. 24, 2015.

Anderson et al.; Reflex principles of immunological homeostasis; Annu. Rev. Immunol.; 30; pp. 313-335; Apr. 2012.

Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Dake; Chronic cerebrospinal venous insufficiency and multiple sclerosis: Hostory and background; Techniques Vasc. Intervent. Radiol.; 15(2); pp. 94-100; Jun. 2012.

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Ellrich et al.; Transcutaneous vagus nerve stimulation; Eur. Neurological Rev.; 6(4); pp. 254-256; 2011 (year of pub. sufficiently earlier than effective US filing date and any foreign priority date).

Gao et al.; Investigation of specificity of auricular acupuncture points in regulation of autonomic function in anesthetized rats; Autonomic Neurosc.; 138(1-2); pp. 50-56; Feb. 29, 2008.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.

Pavlov et al; Controlling inflammation: the cholinergic anti-inflammatory pathway; Biochem. Soc. Trans.; 34(Pt 6); pp. 1037-1040; Dec. 2006.

Peuker; The nerve supply of the human auricle; Clin. Anat.; 15(1); pp. 35-37; Jan. 2002.

Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.

Stevens et al.; The anti-inflammatory effect of some immunosuppressive agents; J. Path.; 97(2); pp. 367-373; 1969 (year of pub. sufficiently earlier than effective US filing date and any foreign priority date).

Tekdemir et al.; A clinico-anatomic study of the auricular branch of the vagus nerve and arnold's ear-cough reflex; Surg. Radiol. Anat.; 20(4); pp. 253-257; Mar. 1998.

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.

Zamotrinsky et al.; Vagal neurostimulation in patients with coronary artery disease; Auton. Neurosci.; 88(1-2); pp. 109-116; Apr. 2001.

Zhao at al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.

Robinson et al.; Studies with the Electrocardiograph on the Action of the Vagus Nerve on the Human Heart; J Exp Med; 14(3):217-234; Sep. 1911.

(56) References Cited

OTHER PUBLICATIONS

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Faltys et al.; U.S. Appl. No. 14/508,940 entitled "Neural stimulation devices and systems for treatment of chronic inflammation," filed Oct. 7, 2014.
Abraham, Coagulation abnormalities in acute lung injury and sepsis, Am. J. Respir. Cell Mol. Biol., vol. 22(4), pp. 401-404, Apr. 2000.
Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.
Antonica, A., et al., Vagal control of lymphocyte release from rat thymus, J. Auton. Nerv. Syst., vol. 48(3), pp. 187-197, Aug. 1994.
Asakura et al., Non-surgical therapy for ulcerative colitis, Nippon Geka Gakkai Zasshi, vol. 98, No. 4, pp. 431-437, Apr. 1997 (abstract only).
Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.
Ben-Noun et al.; Neck circumference as a simple screening measure for identifying overweight and obese patients; Obesity Research; vol. 9; No. 8; pp. 470-477; Aug. 8, 2001.
Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to SHOCK, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression in shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135 (2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova at al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova at al., Vagotomy blocks the protective effects of I.C.V. CNI-1493 against LPS-induced shock, (Supplemental to Shock, vol. 11, 1999, Molecular, cellular, and systemic pathobioligal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, pp. 189-204, (year of pub. Sufficiently earlier than effective US filing date and any foreign priority date) 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cicala et al., "Linkage between inflammation and coagulation: an update on the molecular basis of the crosstalk," Life Sciences, vol. 62(20); pp. 1817-1824, Apr. 1998.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
DAS, Critical advances in spticemia and septic shock, Critical Care, vol. 4, pp. 290-296, Sep. 7, 2000.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Dibbs, Z., et al., Cytokines in heart failure: pathogenetic mechanisms and potential treatment, Proc. Assoc. Am. Physicians. vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Doshi et al., Evolving role of tissue factor and its pathway inhibitor, Crit. Care Med., vol. 30, suppl. 5, pp. S241-S250, May 2002.
Ellington et al., In vitro selection of RNA molecules that bind specific ligands, Nature, vol. 346, pp. 818-822, Aug. 30, 1990.
Esmon, The protein C pathway, Crit. Care Med., vol. 28, suppl. 9, pp. S44-S48, Sep. 2000.

(56) References Cited

OTHER PUBLICATIONS

Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(-)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; (year of pub. sufficiently earlier than effective US filing date and any foreign priority date) 1980.

Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monocluear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Neural regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filing date and any foreign priority date) 2001.
Katagiri, M., et al., Increased cytokine production by gastric mucosa in patients with helicobacter pylori infection, J. Clin, Gastroenterol., vol. 25, Suppl. 1, pp. S211-S214, (year of pub. sufficiently earlier than effective US filing date and any foreign priority date) 1997.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.

(56) References Cited

OTHER PUBLICATIONS

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Krarup et al; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, Shock, vol. 5, No. 5, pp. 385-388, May 1996.

Kuznik, "Role of the vascular wall in the process of hemostatis," Usp Sovrem Biol., vol. 75(1): pp. 61-85, (year of pub. sufficiently earlier than effective US filing date and any foreign priority date) 1973.

Kuznik, et al., "Blood Coagulation in stimulation of the vagus nerve in cats," Biull. Eskp. Biol. Med., vol. 78 (7): pp. 7-9, (year of pub. sufficiently earlier than effective US filing date and any foreign priority date) 1974.

Kuznik, et al., "Heart as an efferent regulator of the process of blood coagulation and fibrinolysis," Kardiologiia, vol. 13(3): pp. 10-17, (year of pub. sufficiently earlier than effective US filing date and any foreign priority date) 1973.

Kuznik, et al., "Role of the heart and vessels in regulating blood coagulation and fibrinolysis," Kagdiologiia, vol. 13 (4): pp. 145-154, (year of pub. sufficiently earlier than effective US filing date and any foreign priority date) 1973.

Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filing date and any foreign priority date) 1973.

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol.Neurosci.; 30; pp. 15-16; (year of pub. sufficiently earlier than effective US filing date and any foreign priority date) 2006.

Lipton, J. M. et al.; Anti-inflammatory actions of the neuroimmunomodulator ?-MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Martindale: The Extra Pharmacopoeia; 28th Ed. London; The pharmaceutical press; pp. 446-485; (year of pub. sufficiently earlier than effective US filing date and any foreign priority date) 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

McGuiness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, (year of pub. sufficiently earlier than effective US filing date and any foreign priority date) 2000.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; (year of pub. sufficiently earlier than effective US filing date and any foreign priority date) 2004.

Mishchenko, et al., "Coagulation of the blood and fibrinolysos in dogs during vagal stimulation," Sechenov Physiological Journal of the USSR, vol. 61(1): pp. 101-107, (year of pub. sufficiently earlier than effective US filing date and any foreign priority date) 1975.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, (year of pub. sufficiently earlier than effective US filing date and any foreign priority date) 1974.

Molina et al., CNI-1493 attenuates hemodynamic and pro-inflammatory responses to LPS, Shock, vol. 10, No. 5, pp. 329-334, Nov. 1998.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79(2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering OnLine, 2(1), pp. 6, Mar. 4, 2003.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Pateyuk, et al.,"Treatment of Botkin's disease with heparin," Klin. Med., vol. 51(3): pp. 113-117, Mar. 1973.

Payne, J. B. et al., Nicotine effects on PGE2 and IL-1 beta release by LPS-treated human monocytes, J. Perio. Res., vol. 31, No. 2, pp. 99-104, Feb. 1996.

Prystowsky, J. B. et al., Interleukin-1 mediates guinea pig gallbladder inflammation in vivo, J. Surg. Res., vol. 71, No. 2, pp. 123-126, Aug. 1997.

Pulkki, K. J., Cytokines and cardiomyocyte death, Ann. Med., vol. 29(4), pp. 339-343, Aug. 1997.

Pullan, R. D., et al., Transdermal nicotine for active ulceratiive colitis, N. Engl. J. Med., vol. 330, No. 12, pp. 811-815, Mar. 24, 1994.

Pulvirenti et al; Drug dependence as a disorder of neural plasticity:focus on dopamine and glutamate; Rev Neurosci.; vol. 12; No. 2; pp. 141-158; Apr./Jun. 2001.

Rahman et al.; Mammalian Sirt 1: Insights on its biological functions; Cell Communications and Signaling; vol. 9; No. 11; pp. 1-8; May 2011.

(56) References Cited

OTHER PUBLICATIONS

Rayner, S. A. et al., Local bioactive tumour necrosis factor (TNF) in corneal allotransplantation, Clin. Exp. Immunol., vol. 122, pp. 109-116, Oct. 2000.
Rinner et al.; Rat lymphocytes produce and secrete acetylcholine in dependence of differentiation and activation; J.Neuroimmunol.; 81(1-2); pp. 31-37; Jan. 1998.
Romanovsky, A. A., et al.,The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, (year of pub. sufficiently earlier than effective US filing date and any foreign priority date) 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, lnflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, (year of pub. sufficiently earlier than effective US filing date and any foreign priority date) 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95, pp. 31-35, (year of pub. sufficiently earlier than effective US filing date and any foreign priority date) 1998.
Sternberg, E. M., Perspectives series: cytokines and the brain 'neural-immune interactions in health and disease,' J. Clin. Invest., vol. 100, No. 22, pp. 2641-2647, Dec. 1997.
Strojnik et al.; Treatment of drop foot using and implantable peroneal underknee stimulator; Scand. J. Rehab. Med.; vol. 19(1); pp. 37R43; (year of pub. sufficiently earlier than effective US filing date and any foreign priority date) 1987.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Sykes, et al., An investigation into the effect and mechanisms of action of nicotine in inflammatory bowel disease, Inflamm. Res., vol. 49, pp. 311-319, Jul. 2000.
Takeuchi et al., A comparision between chinese blended medicine "Shoseiryuto" tranilast and ketotifen on the anit-allergic action in the guinea pigs, Allergy, vol. 34, No. 6, pp. 387-393, Jun. 1985 (eng. abstract).
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J.; Reflex control of immunity; Nat Rev Immunol; 9(6); pp. 418-428; Jun. 2009.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-450; Jun. 2007.
Vanhoutte, et al., Muscarinic and beta-adrenergic prejunctional modulation of adrenergic neurotransmission in the blood vessel wall, Gen Pharmac., vol. 14, pp. 35-37, (year of pub. sufficiently earlier than effective US filing date and any foreign priority date) 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, (year of pub. sufficiently earlier than effective US filing date and any foreign priority date) 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känal, et al., Effects of non-specific ?-adrenergic stimulation and blockade on blood coagulation in hypertension, J. Appl. Physiol., vol. 94, pp. 1455-1459, Apr. 2003.
Von Känal, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

(56) References Cited

OTHER PUBLICATIONS

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-1066; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yeh, S.S. et al., Geriatric cachexia: the role of cytokines, Am. J. Clin. Nutr., vol. 70(2), pp. 183-197, Aug. 1999.

Zhang et al., Tumor necrosis factor, The Cytokine Handbook, 3rd ed., Ed. Thompson, Academic Press, pp. 517-548, Jul. 1, 1998.

Zhang et al.; Roles of SIRT1 in the acute and restorative phases following induction of inflammation.; J Biol Chem.; vol. 285; No. 53; pp. 41391-41401; Dec. 2010.

Diamond et al.; Mapping the immunological homunculus; Proc. Natl. Acad. Sci. USA; 108(9); pp. 3461-3462; Mar. 1, 2011.

Dorr et al.; Effect of vagus nerve stimulation on serotonergic and noradrenergic transmission; J. Pharmacol. Exp. Ther.; 318(2); pp. 890-898; Aug. 2006.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Groves et al.; Recordings from the rat locus coeruleus during acute vagal nerve stimulation in the anaesthetised rat; Neuroscience Letters; 379(3); pp. 174-179; May 13, 2005.

Navzer et al.; Reversing pathological neural activity using targeted plasticity; Nature; 470(7332); pp. 101-104; Feb. 3, 2011.

Neuhaus et al.; P300 is enhanced in responders to vagus nerve stimulation for treatment of major depressive disorder; J. Affect. Disord.; 100(1-3); pp. 123-128; Jun. 2007.

Olofsson et al.; Rethinking inflammation: neural circuits in the regulation of immunity; Immunological Reviews; 248(1); pp. 188-204; Jul. 2012.

Swick et al.; Locus coeruleus neuronal activity in awake monkeys: relationship to auditory P300-like potentials and spontaneous EEEG. Exp. Brain Res.; 101(1); pp. 86-92; Sep. 1994.

Levine et al.; U.S. Appl. No. 14/922,022 entitled "Systems and methods for stimulating and/or monitoring loci in the brain to treat inflammation and to enhance vagus nerve stimulation," filed Oct. 23, 2015.

Cheyuo et al.; The parasympathetic nervous system in the quest for stroke therapeutics; J. Cereb. Blood Flow Metab.; 31(5); pp. 1187-1195; May 2011.

Clark et al.; Enhanced recognition memory following vagus nerve stimulation in human subjects; Nat. Neurosci.; 2(1); pp. 94-98; Jan. 1999.

Tracey et al.; U.S. Appl. No. 14/967,149 entitled "Methods and systems for reducing inflammation by neuromodulation and administration of an anti-inflammatory drug," filed Dec. 11, 2015.

Levine et al.; U.S. Appl. No. 14/968,702 entitled "Extremely low duty-cycle activation of the cholinergic anti-inflammatory pathway to treat chronic inflammation," filed Dec. 14, 2015.

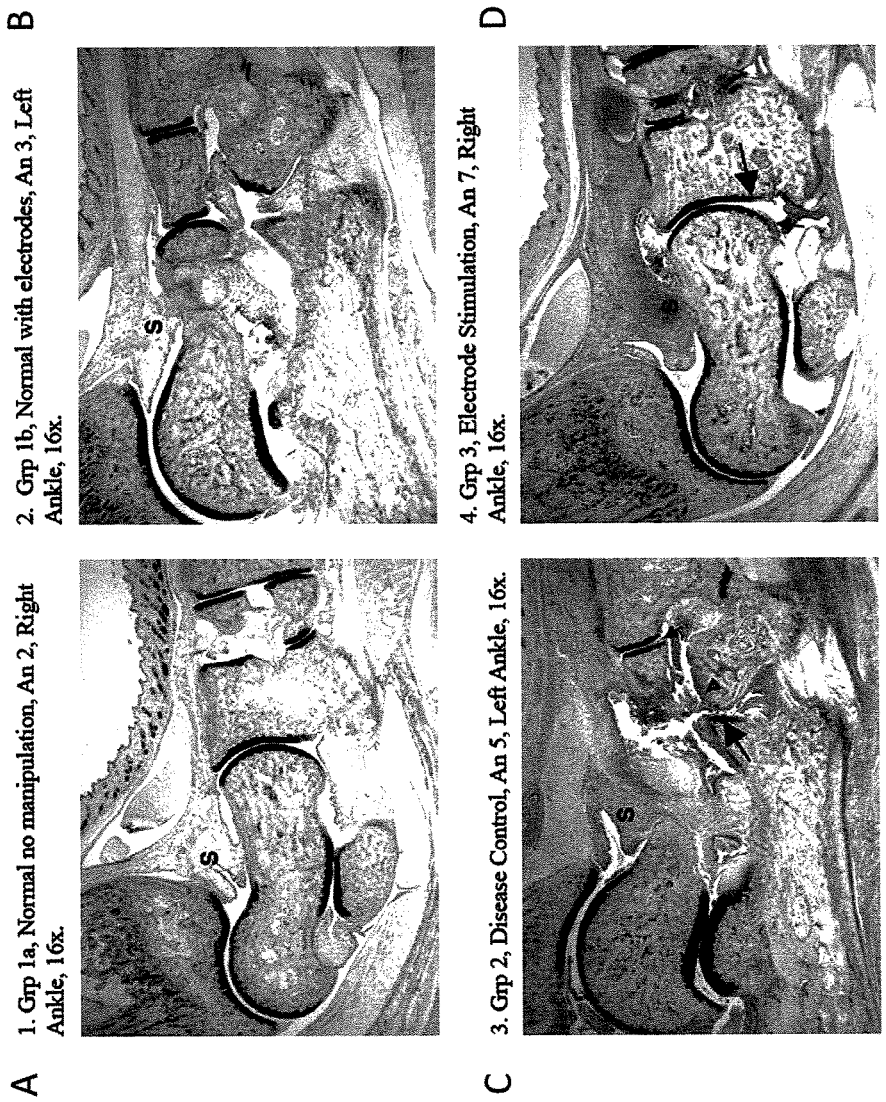
FIGS. 12A-D

FIGS. 13A-D
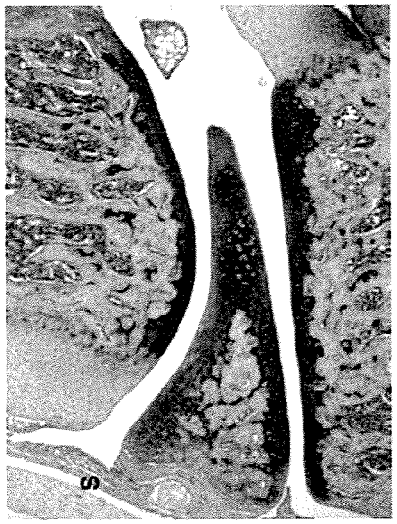
A. 1. Grp 1a, Normal no manipulation, An 1, Right Knee, 50x.
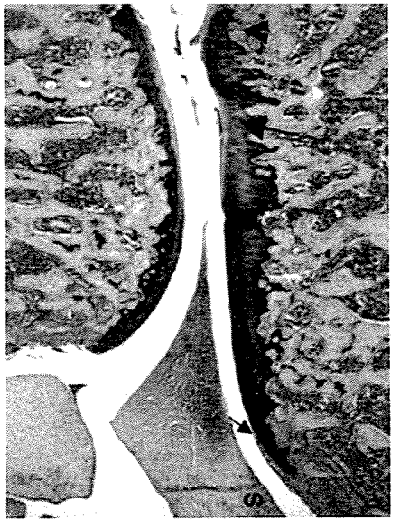
B. 2. Grp 1b, Normal with electrodes, An 1, Left Knee, 50x.
C. 3. Grp 2, Disease Control, An 4, Right Knee, 50x.
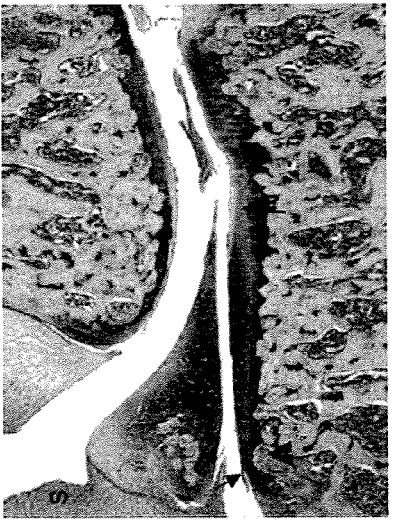
D. 4. Grp 3, Electrode Stimulation, An 8, Left Knee, 50x.

DEVICES AND METHODS FOR MODULATION OF BONE EROSION

CROSS REFERENCE TO RELATED APPLICATIONS

This patent application claims priority to U.S. Provisional Patent Application No. 61/615,777, filed on Mar. 26, 2012, and titled "DEVICES AND METHODS FOR MODULATION OF RANKL, OPG AND OPG/RANKL RATIO". This provisional patent application is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are devices, methods and systems to modulate bone erosion by electrical stimulation of the vagus nerve, including very low duty cycle stimulation of the vagus nerve. These systems and methods may modulate Receptor Activator for Nuclear Factor κB Ligand (RANKL), osteoprotegerin (OPG) and/or RANKL/OPG ratio by modulation of the vagus nerve. In particular, described herein are devices, methods and systems for reducing RANKL and/or increasing the RANKL/OPG ratio by stimulation of the vagus nerve.

BACKGROUND

RANKL is a member of the tumor necrosis factor (TNF) cytokine family that is a ligand for osteoprotegerin, and functions as a key factor for osteoclast differentiation, activation and survival. Targeted disruption of the related gene in mice leads to severe osteopetrosis and a lack of osteoclasts. These deficient mice exhibited defects in early differentiation of T and B lymphocytes, and fail to form lobulo-alveolar mammary structures during pregnancy.

The balance between RANKL, as a principle activator of osteoclast differentiation and activity, and its decoy ligand OPG has been shown to be the primary regulator of bone resorption. RANKL has been further validated as a mediator and biomarker of bone destruction that can be independent of coexisting cartilage damage and inflammation in arthritis.

Modulation of RANKL and/or OPG may therefore be beneficial in treatment of disorders implicated in osteoclast differentiation and/or activity, including bone regulation (e.g., resorption, remolding and/or growth). Suppression or inhibition of RANKL may be therapeutic in a range of other indications as well, including (but not limited to): glucocorticoid-induced and postmenopausal osteoporosis; reduction in bone erosions in rheumatoid arthritis, psoriatic arthritis and other systemic inflammatory diseases; increase in bone mass in patients treated with aromatase inhibitors or androgen deprivation therapy; prevention and treatment of bony metastases in solid tumors and multiple myeloma; and reduction in arterial plaque progression and rupture in atherosclerosis.

Overproduction of RANKL is implicated in a variety of bone diseases, such as rheumatoid arthritis and psoriatic arthritis. RANKL inhibitors (such as denosumab) have been proposed to treat osteoporosis in post-menopausal women. Further, inhibition of RANKL has been examined as a treatment for metastases from a variety of solid tumors and lytic bone lesions in multiple myeloma. For example, metastatic tumor cells may commandeer osteoblasts and other cells in bone to produce RANKL; the tumor cells then uses the resident osteoclasts to breakdown bone matrix and establish metastatic foci and also allow the metastases to grow.

Currently there are a number of pharmacological agents being examined to inhibit RANKL, increase OPG, or increase the OPG/RANKL ratio. For example, as mentioned above, Denosumab is an anti-RANKL antibody that inhibits RANKL. Unfortunately, there are many disadvantages to these therapies, including undesirable side effects and patient compliance. Thus, there is a need for a non-pharmacological therapy to modulate RANKL, OPG and/or OPG/RANKL ratio.

As described in detail herein, the inventors have surprisingly discovered that stimulation of the vagus nerve profoundly and significantly modulates RANKL, OPG and/or OPG/RANKL ratio. Although stimulation of the vagus nerve has been previously described, this is the first time that such stimulation (and particularly electrical stimulation) has been suggested to modulate RANKL.

For example, stimulation of the cholinergic anti-inflammatory pathway (CAP) has been shown to modulate inflammation. CAP is a physiologic regulator of systemic inflammation which utilizes the vagus nerve to reflexively reduce inflammatory responses. Brief, intermittent neurostimulation of the vagus nerve (NCAP) has been shown to be effective in a variety of animal models of acute inflammation (Nature Rev Immunol 2009; 9:418). NCAP using implantable stimulation devices also holds promise as a potential therapeutic approach for chronic human inflammatory diseases. To date, however, the biological pathways affected by NCAP have not implicated RANKL or bone morphology.

For example, US 2006/0178703 to Huston et al. describes treatment of inflammation and inflammatory disorders (including rheumatoid arthritis) by electrical stimulation of the vagus nerve. Although Huston broadly teaches the stimulation of the vagus nerve (including using an implantable stimulator), this references does not optimize the stimulation with respect to osteoprotegerin (e.g., RANKL or OPG).

By targeting the stimulation parameters specific to RANKL/OPG, the methods and devices described herein may avoid potentially undesirable and unnecessary side effects of pharmacological intervention to modulate RANKL/OPG, and may provide for the first time, an implantable, electrical or mechanical devices for modulating RANKL/OPG; non-implantable electrical and mechanical modulation means are also contemplated and described. This data has been prepared using a rodent animal model to examine the effect of vagus stimulation in a rat model, examining bone morphology generally and RANKL/OPG specifically.

SUMMARY OF THE DISCLOSURE

The present invention describes the use of stimulation (e.g., electrical stimulation) to modulate RANKL and/or OPG in a patient. In the examples described herein, a rat animal model was initially used.

As illustrated and described below, a significant reduction in RANKL as well as increases in OPG and OPG/RANKL ratio due to electrical stimulation of the vagus nerve (VNS, vagus nerve stimulation within the specific parameters described herein) is reflected in the 59% reduction in bone resorption, as compared to the sham stimulated group. The reduction in systemic RANKL and increase in OPG/RANKL ratio due to VNS therapy also has implications for protection against the systemic bone loss which often occurs in conjunction with the focal erosions characteristic of rheumatoid arthritis, especially when glucocorticoids are administered. Based on these findings, stimulation of the vagus nerve may be used to inhibit or suppress RANKL, increase OPG and/or increase a patient's OPG/RANKL ratio. Therapeutically, this type of stimulation leading to inhibition or suppression may be used to treat, prevent or ameliorate any disease or disorder for which modulation of RANKL and/or OPG would be beneficial. In particular, as taught herein, any disorder for which pharmacological suppression or inhibition of RANKL and/or OPG (e.g., using a drug such as Denosumab) would be beneficial may be treated by the modulation of the vagus nerve.

For example, described herein is the use of cuff electrodes implanted around a portion of the vagus nerve. In the rat model, cuff electrodes were implanted around the carotid sheath (encompassing the vagus nerve) of female Lewis rats. Up-regulation of RANKL was modeled (induced) as part of a protocol of rat collagen-induced arthritis (CIA). After recovery from the surgical implantation, CIA was induced with intradermal injection of bovine type II collagen and Freund's incomplete adjuvant at days (D) 0 and 6. VNS or sham stimulation was delivered once daily from D9-15 and sacrifice was on D16. Disease progression was monitored by daily caliper measurement of ankle swelling. VNS effect on histological joint damage was assessed using a semi-quantitative scoring method for inflammation, pannus formation, cartilage damage, and bone erosion, using naïve rat (n=4) joints as baseline. Serum cytokines were analyzed at D16.

As a result of this procedure, VNS significantly inhibited bone erosion in rats. Mean ankle diameter of the VNS group (n=9) was significantly lower than that of the unstimulated group (n=12) from D12-16. The average ankle swelling was reduced by 47% over this time period. VNS treatment resulted in significant improvements of all individual ankle score parameters as well as inflammation, pannus formation, and the summed histopathologic scores in knee. Surprisingly, there was a marked reduction in RANKL (80-90%) following once-daily vagus stimulation.

These data provide the first demonstration of the modulation (e.g., suppression) of bone erosion due to stimulation of the vagus nerve such as VNS, as well as the first demonstration of an effect on RANKL and/or OPG due to VNS.

Described herein are devices for modulating bone erosion by low-duty cycle stimulation of the vagus nerve. For example, a device for modulating bone erosion may include: a stimulator element configured to apply stimulation to the vagus nerve; and a controller for repeatedly applying stimulation to the vagus nerve by the stimulator element, wherein the controller is further configured to apply stimulation sufficient to modulate RANKL and/or OPG levels within the patient.

The controller may be configured to apply an extremely low duty-cycle electrical stimulation of between about 0.1 and about 10 mA to the vagus nerve for less than about 2minutes, followed by an off-time of between about 12 and about 48 hours.

Any appropriate stimulator element may be used. In some variations the stimulator is a mechanical stimulator for vibrating the nerve. In some variations, the stimulator element may comprise an electrode configured to apply electrical energy to the vagus nerve. For example, the stimulator element may comprise a nerve cuff configured to apply electrical energy to the vagus nerve.

Also described are methods of reducing bone erosion in a patient at risk for bone loss. For example, the method may comprise applying stimulation to the vagus nerve to reduce RANKL level within the patent. Applying may comprise applying electrical stimulation of between about 0.1 and about 10 mA to the vagus nerve for less than about 2 minutes, followed by an off-time of between about 12 and about 48 hours.

The method may further comprise applying non-invasive stimulation to the vagus nerve.

In some variations the method comprises monitoring a marker related to osteoclast number, activity or number and activity. For example, the method may include determining a level of RANKL within the body.

Also described herein are methods of treating or preventing metastatic cancer comprises applying stimulation to the vagus nerve to reduce RANKL level within a patent at risk for metastatic cancer. The method may further comprise repeatedly applying an extremely low duty-cycle electrical stimulation of between about 0.1 and about 10 mA to the patient's vagus nerve for less than about 2 minutes, followed by an off-time of between about 12 and about 48 hours. The metastic cancer may be breast cancer, prostate cancer, myelomas, or bone cancers.

Also described are methods of treating or preventing rupture of plaques in atherosclerosis, the method comprising repeatedly applying an extremely low duty-cycle electrical stimulation of between about 0.1 and about 10 mA to the patient's vagus nerve for less than about 2 minutes, followed by an off-time of between about 12 and about 48 hours.

The method may also include determining a RANKL level from the patient.

Also described herein are methods of reducing bone erosion within a patient, the method comprising: repeatedly applying electrical stimulation of between about 0.1 and about 10mA to the patient's vagus nerve for less than about 2 minutes, followed by an off-time of between about 12 and about 48 hours; and monitoring a marker related to osteoclast number, activity or number and activity.

In some variations, the method further comprises placing a nerve cuff around a portion of the subject's vagus nerve.

In general, monitoring the marker may comprise monitoring RANKL, OPG or RANKL and OPG.

Any of the methods described may also include administering a drug that inhibits osteoclasts. For example, the drug may be selected from the group consisting of: chloride channel inhibitors (e.g., NS3736), c-src inhibitors (e.g., AZD0530), hormones (e.g., hormone replacement therapy) and selective estrogen-receptor modulators (e.g., raloxifene, lasofoxifene, etc.).

BRIEF DESCRIPTION OF THE DRAWINGS

FIG. 12A-D are photomicrographs of sections through the ankle regions of: (A) a normal, un-manipulated rat; (B) a normal rats in which electrodes were implanted but not stimulated; (C) disease control rats which were un-stimulated; and (D) disease rats in which NCAP (stimulation) was applied as described herein. All of these views were taken through ankle regions at 16× magnification after staining.

FIGS. 13A-D are photomicrographs of sections through the rat knee in: (A) a normal (no manipulation) knee; (B) normal rats in which electrodes were implanted; (C) rats in which arthritis ("disease") was induced but that were not stimulated; and (D) rats in which disease was induced that were stimulated. All of these micrographs were taken at 50× after appropriate staining. FIGS. 13A and 13C are from the right knee, while 13B and 13D are from the left knee.

FIG. 14B shows a comparison between sham and VNS rats looking at TRAP-5B, while

DETAILED DESCRIPTION

Figure 1:
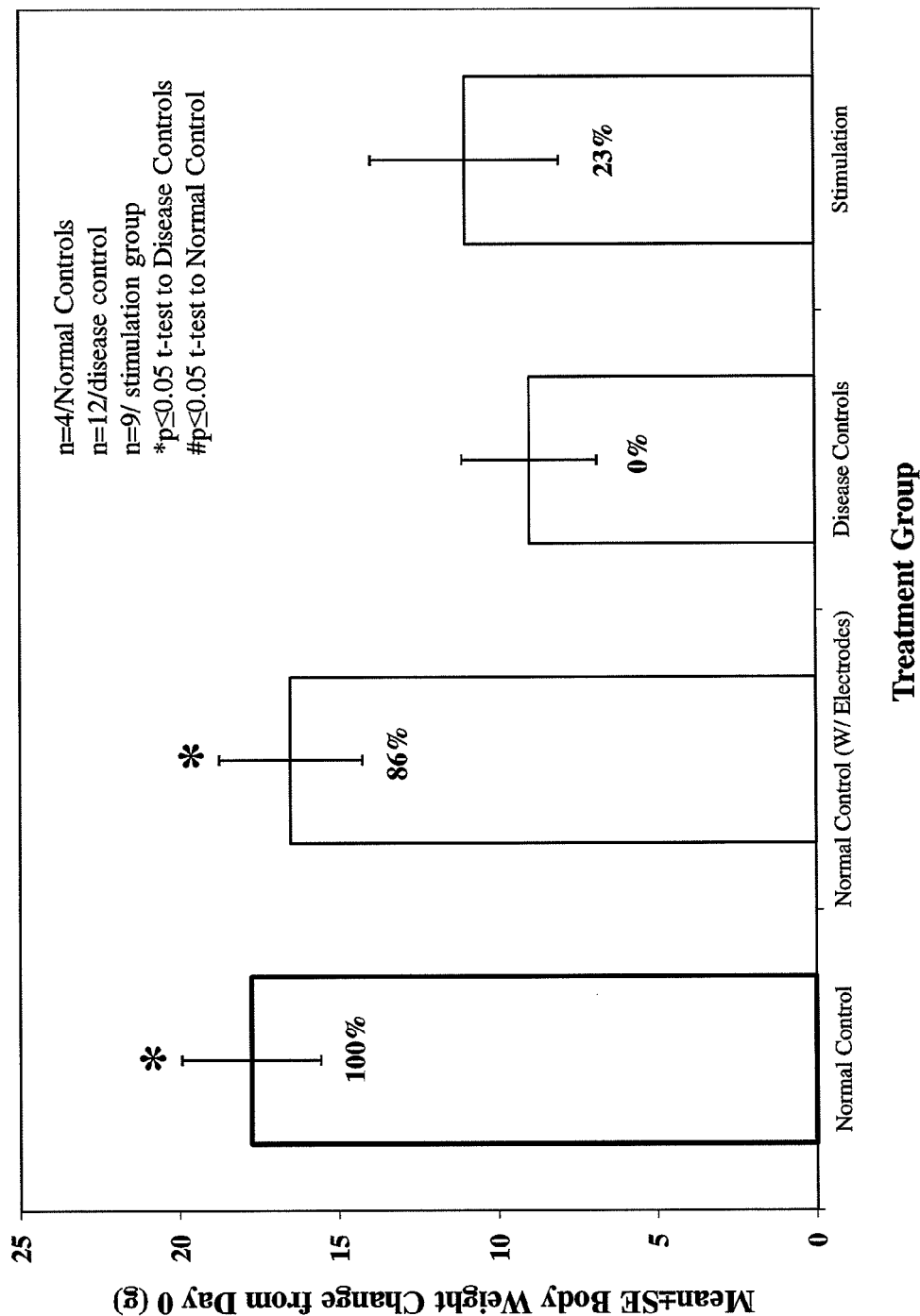
FIG. 1 shows the body weight change from day 0 in rats examined as described herein, over the 16 day period examined, in the normal control, normal control with electrode, disease control, and stimulated test groups. The fractional change between the Disease Controls and Normal Controls are expressed as percentages

Described herein are methods for stimulating the vagus nerve to modulate bone erosion. These methods, devices and systems may also be used to modulate (e.g., reduce, suppress, etc.) RANKL and/or to modulate (increase, enhance, etc.) OPG. The effect of VNS as described herein, and specifically the stimulation parameters described herein, may result in a substantial reduction in bone erosion. Concurrently, the inventors have observed a reduction in RANKL and an increase in OPG compared to sham-treated animals. The modulation of bone erosion resulting from VNS described herein does not necessarily arise from the modulation of RANKL and/or OPG. However, it may also be possible to modulate OPG and/or RANKL using the device and methods described herein, which may be particularly useful in conjunction with other treatments (including pharmacological treatments) which may benefit by modulating RANKL and/or OPG.

In some variations the devices described herein are electrical stimulation devices that may be implanted, and may be activated to apply current for a proscribed duration, followed by a period without stimulation. As described in the examples that follow, the stimulation protocol may comprise a very limited period of stimulation (e.g., an on-time of less than 5minutes, 2 minutes, 1 minute, etc.) followed by an off-time (during which stimulation is not applied, and may be prevented from being applied) of extensive duration (e.g., greater than 12hours, greater than 20 hours, greater than 24 hours, greater than 36 hours, greater than 48 hours, etc). The applied energy may be targeted for a fixed current having a frequency that is within the range of 0.5 mA to 5 mA (e.g., approximately 3 mA), at a frequency of between about 1 Hz and about 100 Hz (e.g., 10 Hz), where the pulses applied have a pulse width of approximately (50-500usec, e.g., a 200 usec pulse). Thus, the duty-cycle of the applied current may be extremely low, where duty cycle may refer to the ratio of on-time/(on-time plus off-time). The stimulation is applied at an extremely low duty cycle, where duty cycle may refer to the percent of on-time to the total on-time and off-time for the ongoing treatment. The effect may be seen relatively quickly, and may persist.

For example, we show herein that a low level, low duty cycle stimulation protocol (as described herein) suppresses bone erosion. Further, a low level, low duty cycle stimulation protocol (as described herein) suppresses RANKL level in blood sampled from a stimulated subject. We herein show the effectiveness of low level, low duty cycle stimulation administered over an entire week. This type of stimulation contrasts with the use of a high duty cycle stimulation used by others to modulate vagus-nerve mediated functions (such as heart rate, etc.), or treat disorders such as epilepsy and depression. An important finding here is that RANKL can be suppressed/reduced. This effect is corroborated at these low duty cycle parameters by examining the histology of the bone, showing a significant reduction in bone resorbption.

The methods, devices and systems herein may be applied specifically to treat any disorder for which a reduction or suppression of RANKL would be beneficial, including treatment of bone degeneration (e.g., rheumatoid arthritis, osteoporosis, etc.) and/or other disorders implicating bone resorption and/or osteoclasts. For example, described herein are electrodes (e.g., cuff electrodes) that may be placed around the vagus nerve and may communicate with one or more stimulators configured to apply appropriate stimulation of the vagus nerve to modulate bone erosion and/or RANKL/OPG. The stimulator may be implanted. In some variations the stimulator is integral to the electrodes, and may be charged externally. The extremely low duty-cycle of the technique described herein may allow the device to be miniaturized to a greater degree than previously suspected for the treatment of chronic disorders via an implantable device.

EXAMPLE ONE

Treatment of Rats Via Cuff Electrode

Figure 11A:
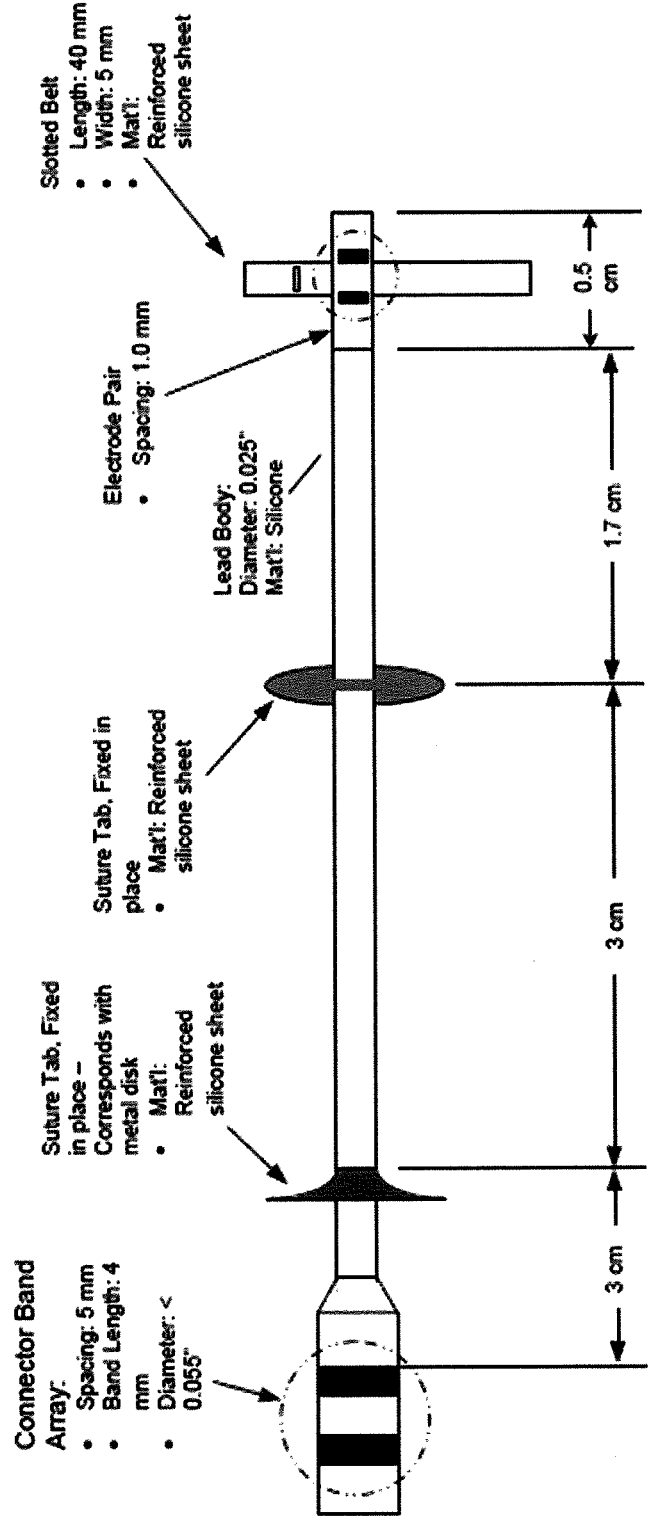
FIG. 11A illustrates one variation of a cuff electrode as described herein.
Figure 11C:
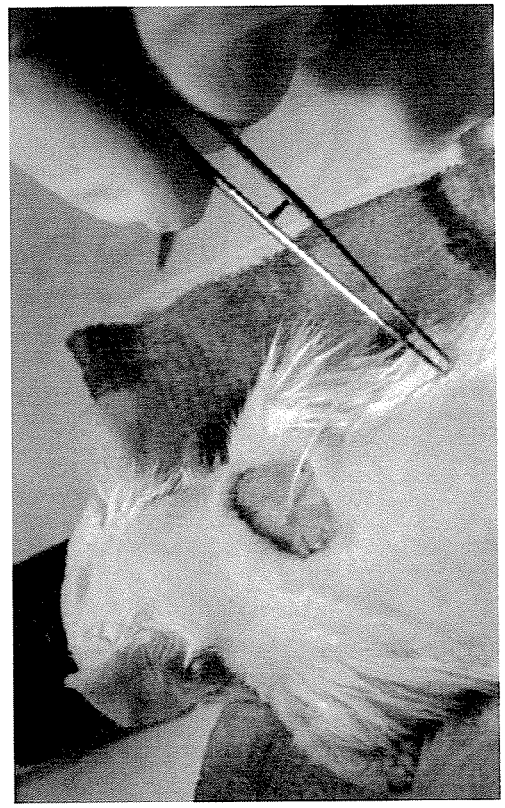
FIGS. 11B and 11C illustrate application of the cuff electrode example shown in FIG. 11A.
Figure 11B:

One variation of a cuff electrode (shown in FIG. 11A) was implanted in rats and compared to control animals in a model of induced arthritis. Rats were anesthetized (e.g., with intramuscular injection of Ketamine (100 mg/kg)/Xylazine (10 mg/kg)) and secured in supine position. FIGS. 11B and 11C illustrate one example of the procedure. A ventral midline cervical incision was made between the mandible and sternum. The subcutaneous tissue was dissected and retracted laterally. The mandibular salivary glands were bluntly separated and retracted laterally, and the left carotid sheath was isolated between the sternomastoid and sternohyoid muscles. A custom-built bipolar cuff electrode (illustrated in FIG. 11A) with a silicone coated platinum wire lead was secured about the carotid sheath containing the vagus nerve and tightened manually with a belt. This cuff electrode was implanted. The belt was then fastened with suture. The lead was secured to the left sternomastoid with suture, providing slack in the wire to the cuff to prevent displacement. The rat was then turned to a prone position and a 2 cm dorsal midline incision was made between the scapulae. A tunnel was created and the distal end of the electrode pulled through and positioned sub-dermally. The lead was secured to the trapezius with suture. The skin on the neck and back was sutured tightly with running suture. The rats were given subcutaneous saline for resuscitation and recovered in their cages (single rat/cage). The rats recovered from surgery for 14 days. The leads were externalized through a small incision on the back and the rats were then jacketed, securing the externalized lead. The rats acclimated to the jackets for 5 days before type II collagen arthritis treatment.

Four groups of rats were examined as part of this analysis: control (unoperated/untreated) rats, or "normal" rats; normal rats with implanted cuff electrodes; disease control rats were treated with rat collagen; and diseased treated rats, which were rats with implanted cuff electrodes that were electrically stimulated as described herein.

| Group # | Name | Implantation | CIA |
|---|---|---|---|
| 1a | Normal Controls | N | N |
| 1b | Normal Control (W/Electrodes) | Y | N |
| 2 | Disease Controls | Y | Y |
| 3 | Stimulation | Y | Y |

Vagus nerve stimulation in animals with implanted cuff electrodes was performed after confirming the impedances between the contacts of the sheath were checked to ensure good contact and a closed circuit. Electrical stimulus was applied using a fixed current (in a range of between 0-3000 µA) at 10 Hz, 200 µsec pulse. Current was applied through the cuff electrode. These stimuli were generated by a current source stimulator running under custom software. By optimizing the level of current applied, a stimulation protocol of 3000 uA, at 10 Hz, 200 usec pulse, for 60 second duration, simulating 1×/day (e.g., on-time of 60 sec/24 hours) on the Lewis rats was used. The pulse applied was a biphasic square pulse, each phase was 200 usec, with a 50 usec interpulse duration. Voltage ranged due to constant current requirements.

In FIGS. 1-10B, the test subject animals received type II collagen arthritis treatment (intradermal injection of bovine type II collagen and Freunds incomplete adjuvant at days 0 and 6). NCAP or sham stimulation was delivered as described above (e.g., once a day for 1 min), beginning on day 9, continuing through day 15. During the course of the procedure, animals were monitored to track the effect on markers of arthritis, including ankle diameter and paw weight. After 16 days, animals were sacrificed and assayed for inflammatory markers and markers of arthritis.

Measurements of serum proteins (e.g., RANKL, OPG) were performed. Samples were measured in quadruplicate at a 2× dilution. Data shown in the figures are expressed as means or as percentage of level observed in unstimulated disease control group.

Results

Figure 2:
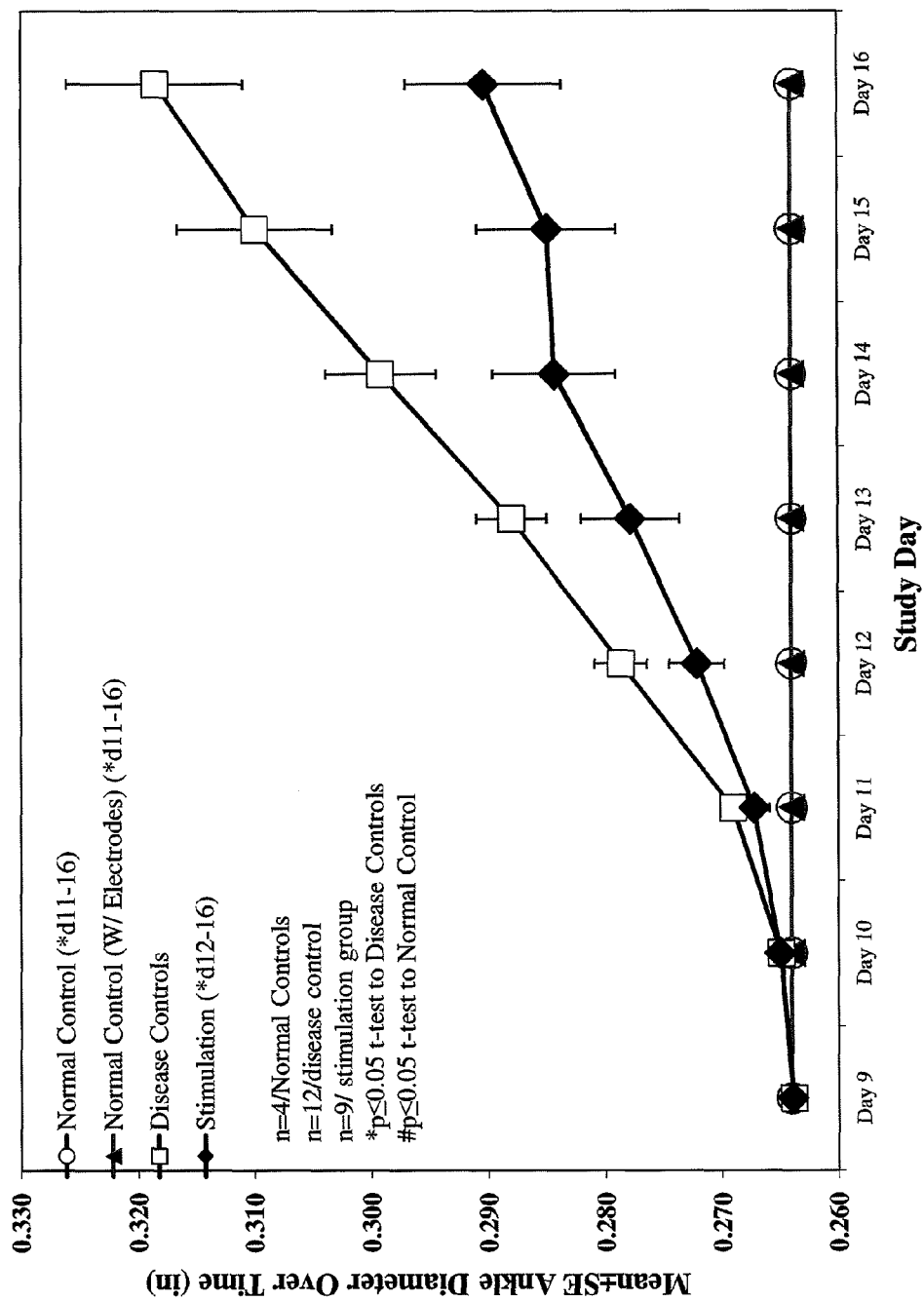
FIG. 2 shows the change in rat ankle diameter over time in the normal control, normal control with electrode, disease control, and stimulated test groups.
Figure 3:
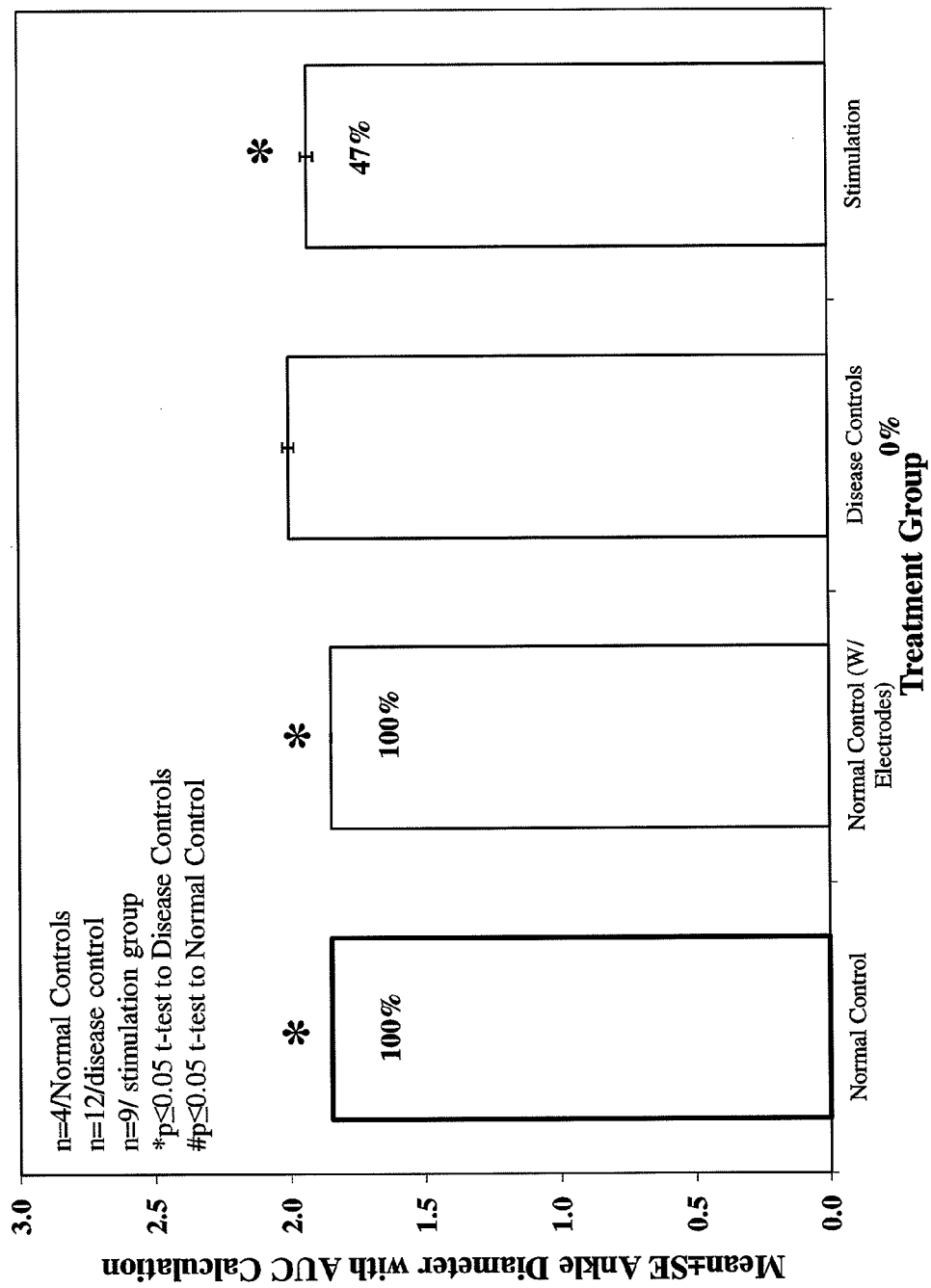
FIG. 3 shows ankle diameter in the normal control, normal control with electrode, disease control, and stimulated test groups. The fractional change between the Disease Controls and Normal Controls are expressed as percentages
Figure 4:
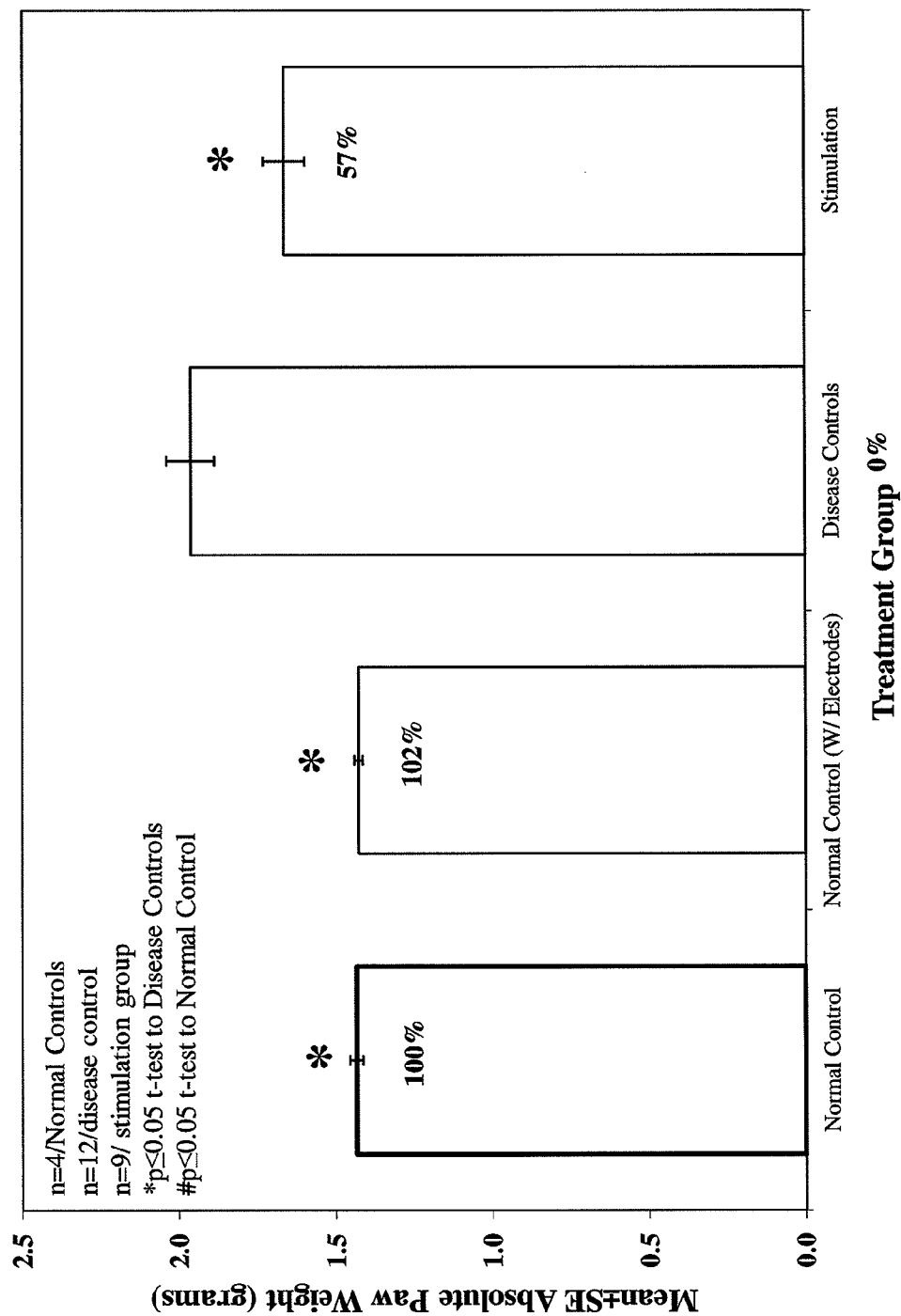
FIG. 4 shows absolute paw weight at day 16 for the normal control, normal control with electrode, disease control, and stimulated test groups. The fractional change between the Disease Controls and Normal Controls are expressed as percentages FIG. 5 compares the ankle histopathology scores between the disease control group and the stimulation group after day 16.

As mentioned, FIGS. 1-10B illustrate the results of the animal trials at the stimulation levels described above. For example, FIG. 2 illustrates the effect of stimulation in reducing one indicator of arthritis, ankle diameter, over time. FIG. 3 shows another variation of this data, in which the change in ankle diameter is represented as a bar graph. Another indicator of arthritis is paw weight. FIG. 4 shows the effect of stimulation as described above on the absolute paw weight of the rat. There is a significant inhibition in the increase in paw weight compared to the diseased control group.

Figure 5:
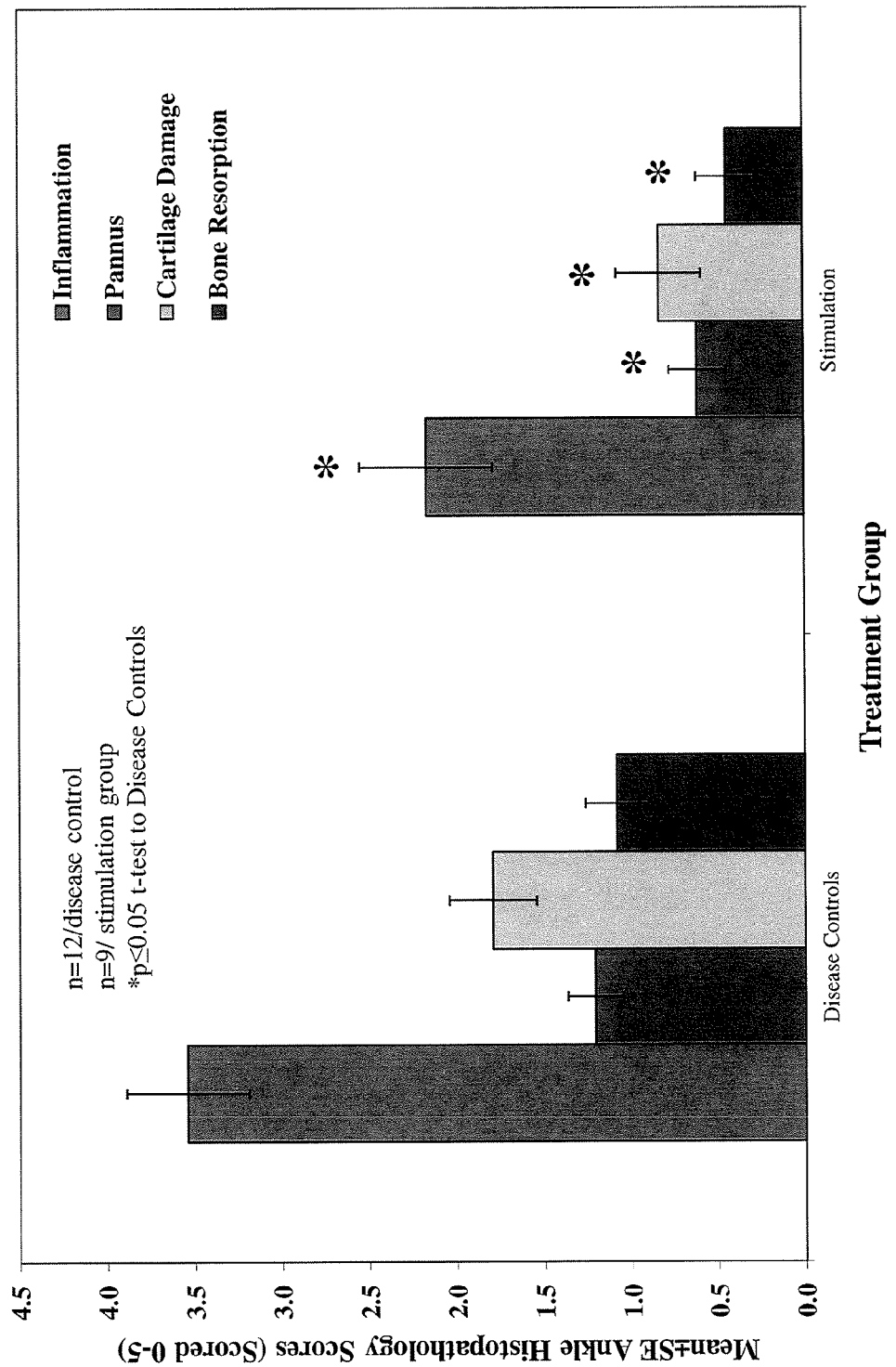

An examination of the histopathology of the control, diseased and stimulated rats was performed (e.g., see FIGS. 12A-D). A quantitative analysis of this data is shown for each of four different indices (inflammation, pannus, cartilage damage and bone resorption) in FIG. 5 comparing disease controls with rats that were stimulated as described above. Appropriate stimulation of the vagus nerve results in a significant reduction in all four of these indicators, consistent with the gross indicators described above. The final column in each cluster of columns shows bone resorption, which was significantly decreased following stimulation of the vagus nerve, as discussed above.

Figure 6:
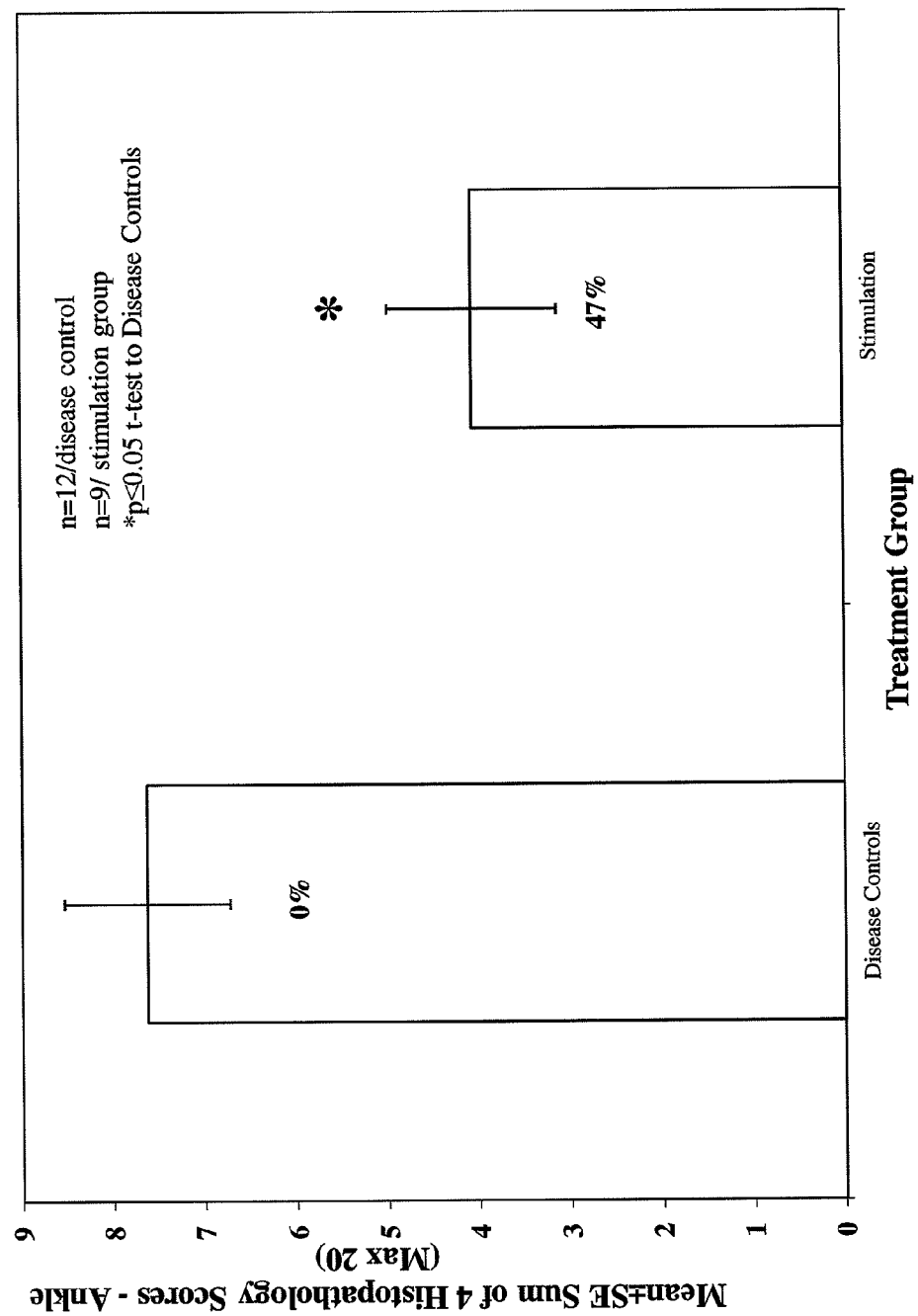
FIG. 6 compares the sum of the four ankle histopathology scores between the disease control and the stimulation groups after day 16. The fractional change between the Disease Controls and Normal Controls (not shown) are expressed as percentages.
Figure 7:
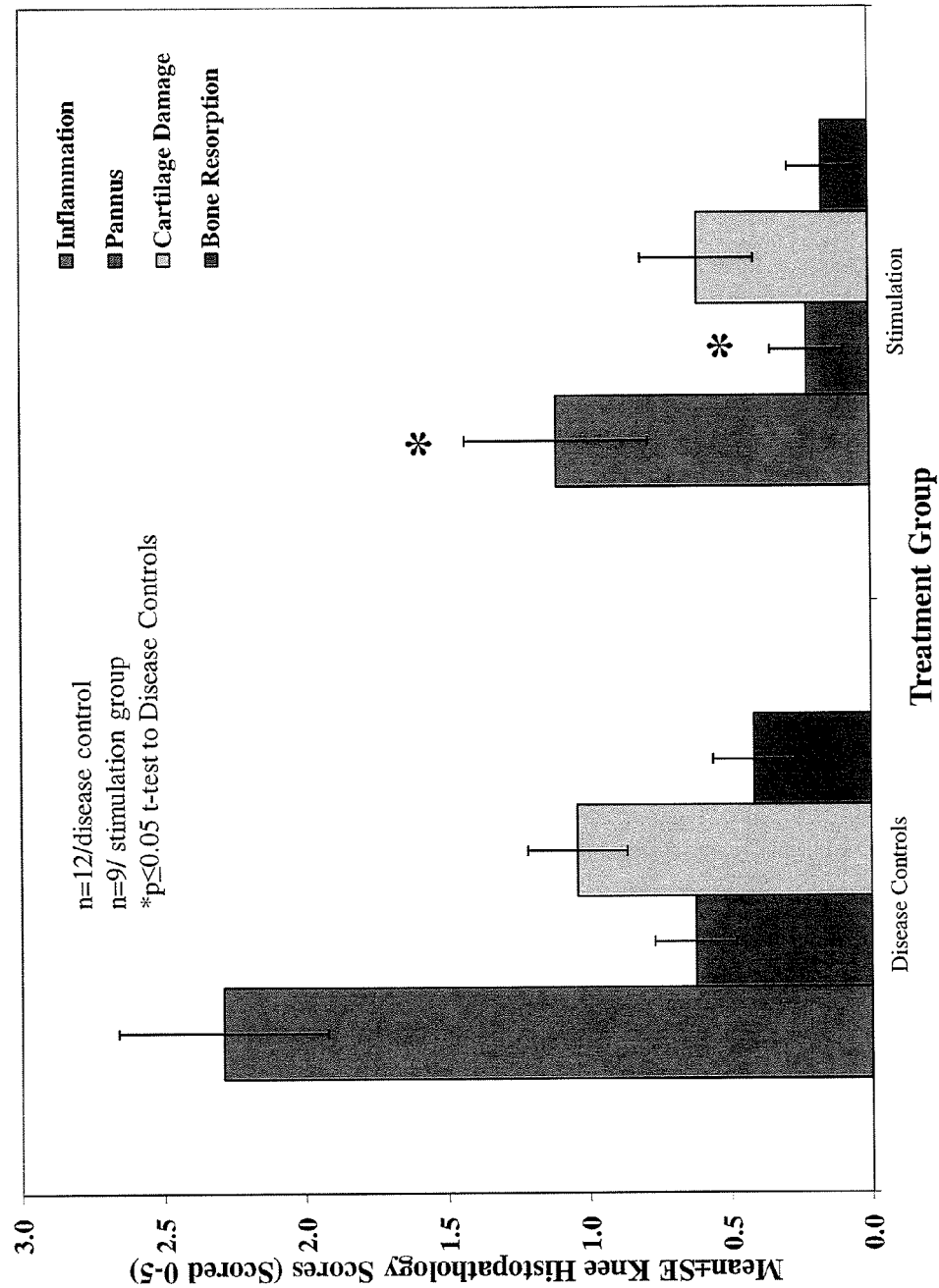
FIG. 7 compares the knee histopathology scores between the disease control group and the stimulation group after day 16.
Figure 8:
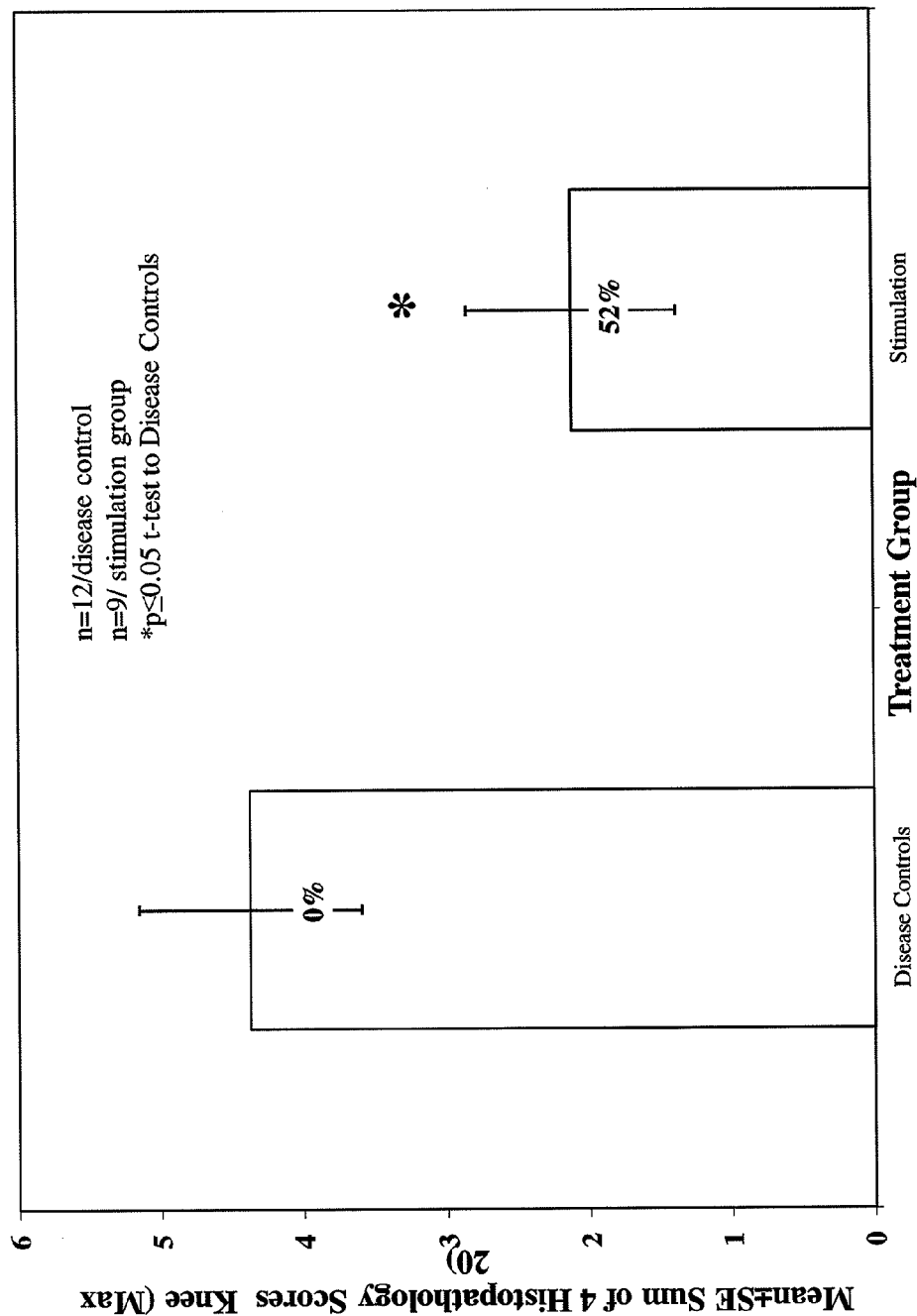
FIG. 8 compares the sum of the four knee histopathology scores between the disease control group and the stimulation group after day 16. The fractional change between the Disease Controls and Normal Controls (not shown) are expressed as percentages.

FIG. 6 simplifies this data, showing two bar graphs, each representing the sum of the histopathology scores. FIGS. 7, 8 and 13A-D show similar results examining the histopathology taken from the rat knee. Again, bone resorption was substantially decreased, consistent with a suppression or reduction of RANKL and/or increase in OPG as a result of electrical stimulation.

Figure 9A:
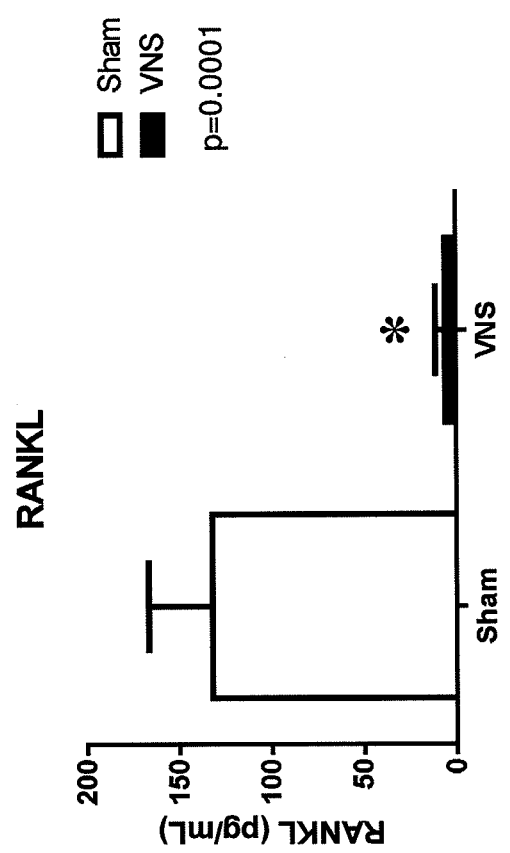
FIG. 9A shows the significant reduction in RANKL as well as increases in OPG and OPG/RANKL ratio due to NCAP.
Figure 9B:
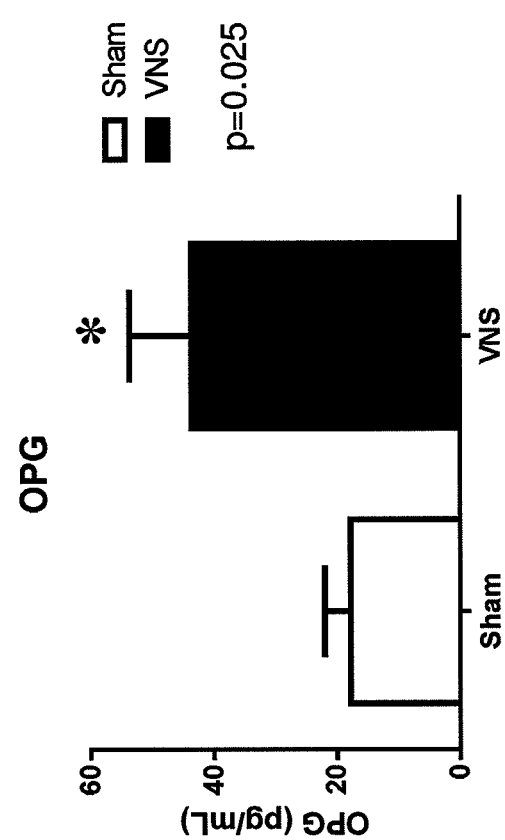
FIG. 9B shows the concomitant significant increase in OPG.
Figure 10B:
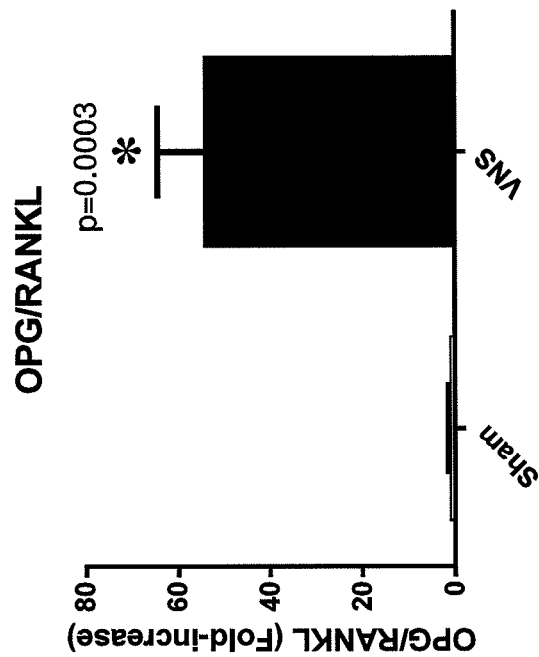
FIG. 10B shows the fold-increase in OPG/RANKL ratio between sham and vagus nerve stimulated rats.
Figure 10A:
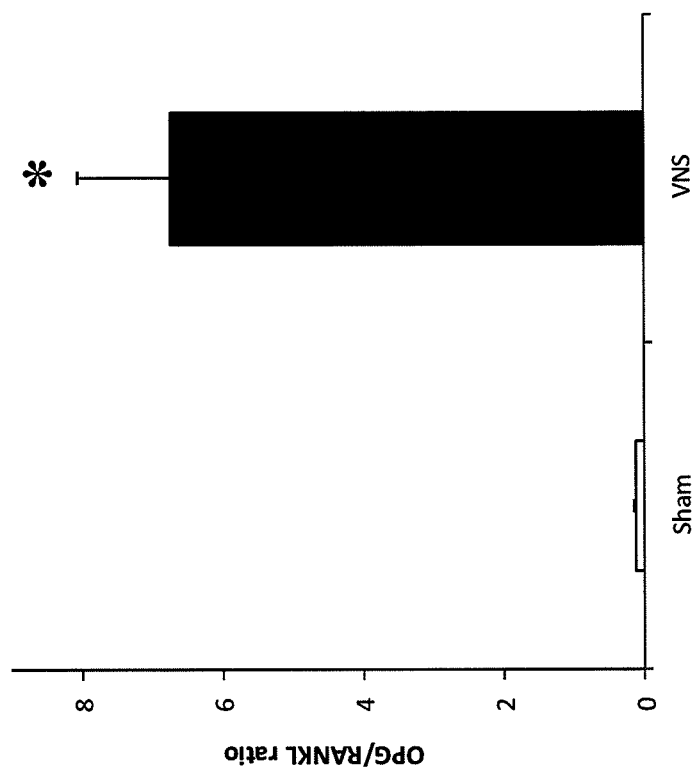
FIG. 10A shows the dramatic difference in OPG/RANKL ratio in sham versus vagus nerve stimulation rats. Similarly

Surprisingly, vagus stimulation decreased levels of RANKL and increased levels of OPG in the serum, as shown in FIGS. 9A-10B. For example, the decrease or suppression of RANKL is directly seen when looking at levels of RANKL from blood taken from control and treated animals, as illustrated in FIG. 9A. As mentioned, receptor activator of nuclear factor κB ligand (RANKL) has a crucial role in promoting bone resorption and is antagonized by osteoprotegerin (OPG). These biomarkers have been shown to correlate with ongoing joint damage in rheumatoid arthritis. To determine whether NCAP could also result in an improvement in key clinical biomarkers of arthritis progression and therapy, terminal serum samples were analyzed for levels of RANKL and OPG. Biomarker analysis on serum RANKL and OPG was performed by ELISA (Cusabio, China) with plasma from terminal bleed according to manufacturer's specification. Samples that fell below the lower limit of detection (LLD) were assigned a value of 1 pg/ml less than the LLD (RANKL=4 pg/mL, OPG=6 pg/mL). Relative to CIA, Sham Stimulation, QD vagus nerve stimulation reduced RANKL concentration by 95% (NCAP=6±2 Vs. Sham=132±13; p=0.01) and increased OPG concentration by 145% (NCAP=44±10 Vs. Sham=18±4; p=0.02), as shown in FIGS. 9a and 9b. In addition, the OPG/RANK ratio is significantly increased in the vagus nerve stimulation group relative to the sham stimulation group (NCAP=6.8±1.3 Vs. Sham=0.1±0.1; p=0.01), representing a 54-fold increase with respect to sham, as shown in FIGS. 10a and 10b.

Figure 11D:
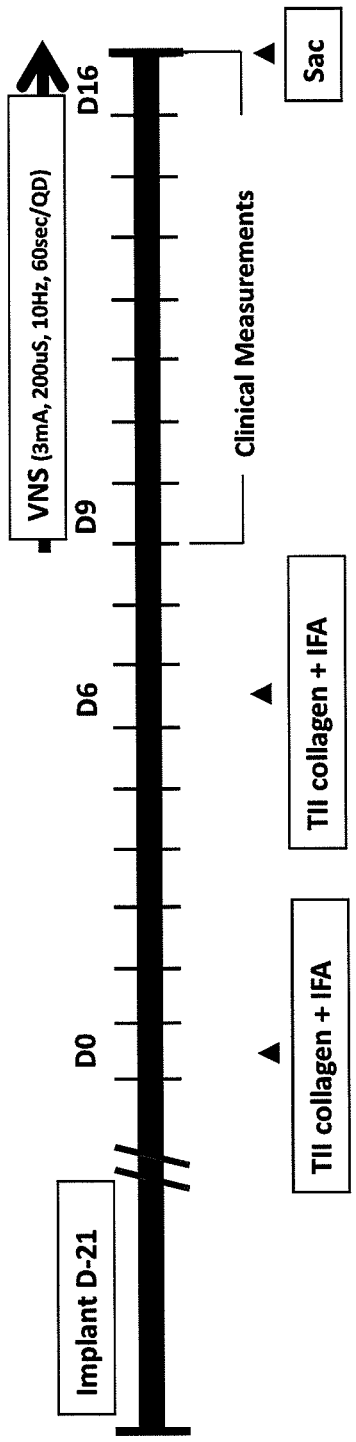
FIG. 11D illustrates the method of inducing the model of arthritis in rats used in some of the examples illustrated.

As briefly described above, FIGS. 12A-D show photomicrographs taken through: the ankle of a normal control animal (FIG. 12A) ("S" indicates synovium); the ankle of a normal control animal with an electrode implanted (FIG. 12B); the ankle of a control animal in which an arthritis-like diseased state (e.g., induced by injection of collagen as illustrated in FIG. 11D and described above) has been induced (FIG. 12C); and the ankle of an animal with induced arthritis-like disease that received electrode stimulation as described above. The disease-induced ankles in FIG. 12C show marked inflammation and synovitis (S) and mild cartilage damage (large arrows) with minimal pannus (small arrows) and bone resorption (arrowhead). In contrast, the ankle from the animal that received electrical stimulation in FIG. 12D shows mild inflammation and synovitis (S) and minimal cartilage damage (large arrow) with minimal pannus (small arrows).

Similarly, FIGS. 13A-D show micrographs through sections of the knees of: a normal control animal (FIG. 13A); a normal control animal with electrode stimulation (FIG. 13B); a disease control animal (FIG. 13C); and a diseased animal that received electrode stimulation (FIG. 13D). The disease control animal showed severe inflammation and synovitis (S) and moderate cartilage damage (large arrow) with mild pannus (small arrow) and bone resorption (arrowhead). In contrast the diseases animal that received stimulation (shown in FIG. 13D) had severe inflammation and synovitis (S) and moderate cartilage damage (large arrow) with mild pannus (small arrow) and bone resorption (arrowhead).

Systems and Devices

In general, a device or system for modulating RANKL and/or OPG may include a stimulator element (e.g., an electrode, actuator, etc.) and a controller for controlling the application of stimulation by the stimulator element. A stimulator element may be configured for electrical stimulation (e.g., an electrode such as a cuff electrode, needle electrode, paddle electrode, non-contact electrode, array or plurality of electrodes, etc.), mechanical stimulation (e.g., a mechanical actuator, such as a piezoelectric actuator or the like), ultrasonic actuator, thermal actuator, or the like. In some variations the systems and/or devices are implantable. In some variations the systems and/or device are non-invasive. In general, the controller may include control logic (hardware, software, firmware, or the like) to control the activation and/or intensity of the stimulator element. The controller may control the timing (e.g., on-time, off-time, stimulation duration, stimulation frequency, etc.). In variations in which the applied energy is electrical, the controller may control the applied waveform (amplitude, frequency, burst duration/inter-burst duration, etc.). Other components may also be include as part of any of these device or system, such as a power supply (e.g., battery, inductive, etc.), transmit/receive elements (e.g., antenna, encoder/decoder, etc.), signal generator (e.g., for conditioning or forming the applied signal waveform), and the like.

In one example, an implantable device for modulating RANKL and/or OPG includes an electrode for electrically stimulating the vagus nerve. The electrode may be, for example, a cuff electrode. The electrode may be connected (directly or via a connector) to a controller and signal generator. The signal generator may be configured to provide an electrical signal to the electrode(s). For example, the electrical signal may be an electrical waveform having a frequency of between about 0.1 Hz and about 1 KHz (e.g., 10 Hz), where the pulses applied have a pulse width of approximately (50-500 usec, e.g., a 200 usec pulse). The signal generator may be battery (and/or inductively) powered, and the electrical signal may be amplitude and/or voltage controlled. For example in some variations the device or system may be configured to apply a current that is between about 0.05 mA to 25 mA (e.g., approximately 0.5 mA, 1 mA, 3 mA, etc.). The electrical signal may be sinusoidal, square, random, or the like. In generally the controller (which may be embodied in a microcontroller such as a programmed ASIC), may regulate turning on and off the stimulation. For example, stimulation may be applied for an on-time of between about 0.1 sec and 10 minutes (e.g., between 1 sec and 5 minutes, between 1 sec and 2 minutes, approximately 1 minute, etc.); the stimulation may be configured to repeat automatically once every other day (off time of approximately 48 hours), once a day (e.g., with an off-time of approximately 24 hours), twice a day (off-time of approximately 12 hours), three times a day (off time of approximately 8 hours), four times a day (off time of approximately 6 hours), or the like. In some variations the implant may be configured to receive control information from a communications device. The communications device may allow modification of the stimulation parameters (including off-time, on-time, waveform characteristics, etc.).

In use, an implant may be configured to be implanted so that the electrodes contact or approximate the vagus nerve or a portion of the vagus nerve. In one variation the implant includes a cuff that at least partially surrounds the vagus (e.g., near the carotid region). The controller and/or signal generator (including any power source) may be formed as part of the cuff or may be connected to by a connector (e.g., wire).

In some variations the device may be non-invasive. For example, the device may be worn outside the body and may trigger stimulation of the vagus nerve from a site external to the body (e.g., the ear, neck, torso, etc.). A non-invasive device may include a mechanical device (e.g., configured to apply vibratory energy). In some variations the device is configured to apply ultrasound that may specifically target the vagus nerve and apply energy to activate the vagus nerve. In some variations, transcutaneous magnetic stimulation of the vagus nerve may be used.

In any of the variations described herein, the devices, system and methods may be configured to prevent desensitization of the signal in a way that would reduce or inhibit the modulation bone erosion and/or of RANKL and/or OPG. For example in some variations, "over stimulation" of the vagus nerve, e.g., simulation at intensities that are too great or applied for too long, or outside of the frequency ranges described herein, may result in desensitization of the effect, thus further modulation may be limited or inhibited.

The examples illustrated above may provide insight into the devices, systems and methods of use for stimulation of the vagus nerve to modulate bone erosion and/or RANKL and/or OPG. These methods and devices may be used to treat any indication for which modulation of osteoclasts would be beneficial. Non-limiting examples of indications include rheumatoid arthritis, osteoarthritis, psoriatic arthritis, certain cancers (e.g., breast cancer, prostate cancer, myelomas, bone cancers), atherosclerosis (e.g., to prevent rupture of atherosclerotic plaques), etc. In general, these devices may offer alternative and in some ways superior treatment as compared to pharmacological interventions aimed at modulating RANKL and/or OPG, and therefore may be used for any indication for which such pharmacological treatments are suggested or indicated.

Thus, the methods of modulating bone erosion as described herein may be used in conjunction with one or more pharmacological interventions, and particularly interventions that treat bone erosion and related disorders or conditions. The methods described herein, which have been shown to modulate RANKL and OPG, may potentiate other treatments, and particularly those that effect the activity of osteoclasts. For example, it may be beneficial to treat a subject receiving stimulation of the vagus nerve to modulate bone erosion by also providing agent such as a chloride channel inhibitors, c-src inhibitors, hormones (e.g., hormone replacement therapy) and selective estrogen-receptor modulators (SERM). As the vagal stimulation already modulates the RANKL/OPG ratio, further modulation of osteoclast differentiation may not be necessary, though in some variations agents that effect differentiation may be potentiated by this treatment.

Thus, described herein are devices (VNS devices) for the treatment of bone erosion. Such devices are generally configured to apply low duty-cycle stimulation to the vagus nerve of a subject, as described in any of the variations (or sub-combinations) of these variations.

In use, any of the methods described herein may include a step of monitoring osteoclasts, which may include osteoclast numbers and/or activity, and/or differentiation. Osteoclasts may be monitored directly (e.g., by histology, imaging, etc.) or indirectly by one or more markers correlated or correlatable with osteoclast number, genesis and/or activity, including RANKL, OPG, TRAP-5B, CTX-1, cathespsin K, or any other appropriate marker, including markers for resorption (e.g., NTX/DpD, etc.). Monitoring may be continuous or discrete (e.g., at one or more times, or time intervals).

Figure 16:
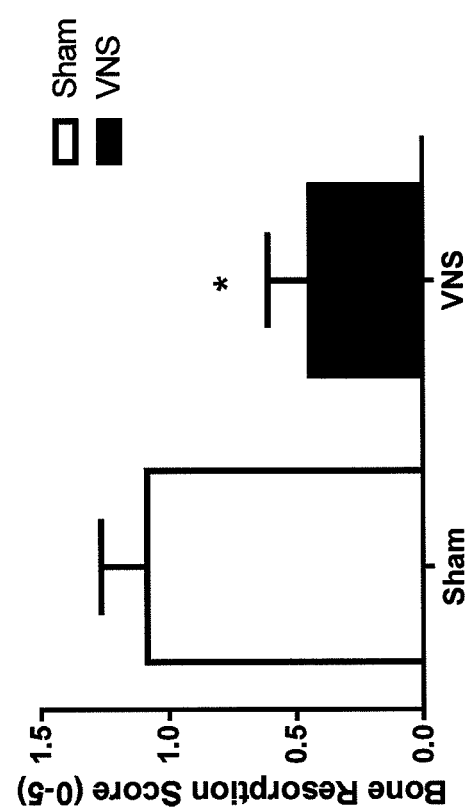
FIG. 16 illustrates the reduction in bone erosion (bone resorption) in the animals stimulated with VNS compared to sham.

The information described herein for the first time shows that stimulation of the vagus nerve modulates bone erosion. This is seen directly in the mouse model, as described above in FIGS. 1-5. FIG. 16 extracts the data specific to bone erosion between sham and rats receiving VNS. In FIG. 16, preserved and decalcified (5% formic acid) ankle joints were cut in half longitudinally, processed through graded alcohols and a clearing agent, infiltrated and embedded in paraffin, sectioned, and stained with Toluidine Blue (T. blue) by Bolder BioPATH, Inc. associated personnel. Tissues from all animals were examined microscopically by a board certified veterinary pathologist and observations were entered into a computer-assisted data retrieval system. In FIG. 16, the scoring of Joints Bone Resorption from the ankle was ranked as 0 (Normal), 1 (Minimal, small areas of resorption, not readily apparent on low magnification, rare osteoclasts), 2 (mild, with more numerous areas of resorption, not readily apparent on low magnification, osteoclasts more numerous, <¼ of tibia at edges is resorbed), 3 (moderate, with obvious resorption of medullary trabecular and cortical bone without full thickness defects in cortex, loss of some medullary trabeculae, lesion apparent on low magnification, osteoclasts more numerous, ¼ to ⅓ of tibia affected, smaller tarsals affected), 4 (marked, full thickness defects in cortical bone, often with distortion of profile of remaining cortical surface, marked loss of medullary bone, numerous osteoclasts, ½-¾ of tibia affected, destruction of smaller tarsals) and 5 (severe, full thickness defects in cortical bone, often with distortion of profile of remaining cortical surface, marked loss of medullary bone, numerous osteoclasts, >¾ of tibia affected, severe distortion of overall architecture).

Figure 14A:
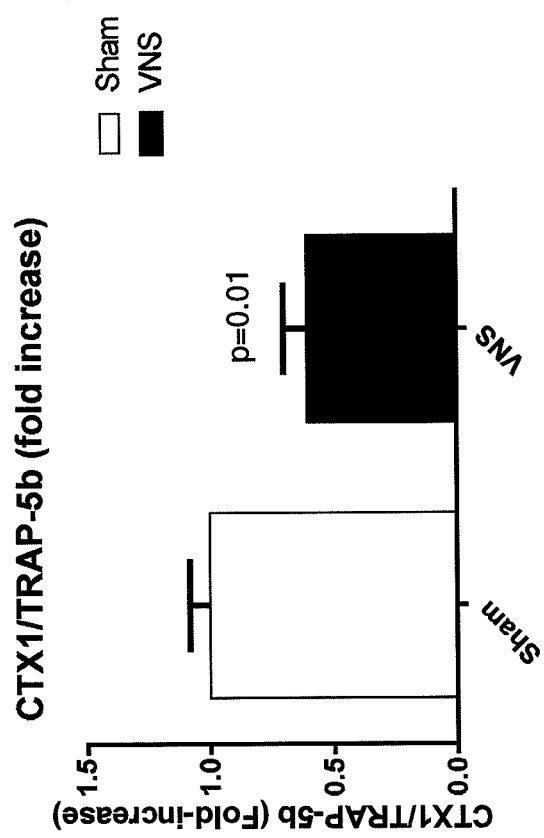
FIG. 14A illustrates a significant decrease in CTX/TRAP-5B compared to sham. CTX and TRAP-5B are surrogate markers for osteoclast activity (CTX), and number (TRAP-5B), respectively.

In FIG. 16, it is clear that relatively low duty-cycle (infrequent ongoing) stimulation of the vagus nerve in the rats results in a significant reduction in bone erosion compared to sham-stimulated animals receiving the same type II collagen arthritis treatment, which otherwise results in bone erosion. Additional markers for activity of osteoclasts were also examined consisted with the modulation of bone erosion seen with VNS. For example, FIG. 14A shows the ration of CTX1/TRAP-5b from serum taken from a terminal draw (>D16) of animals undergoing the rat collagen-induced arthritis protocol (e.g., FIG. 11D). CTX1/TRAP-5B may be referred to a measure of osteoclast activity.

Figure 14C:
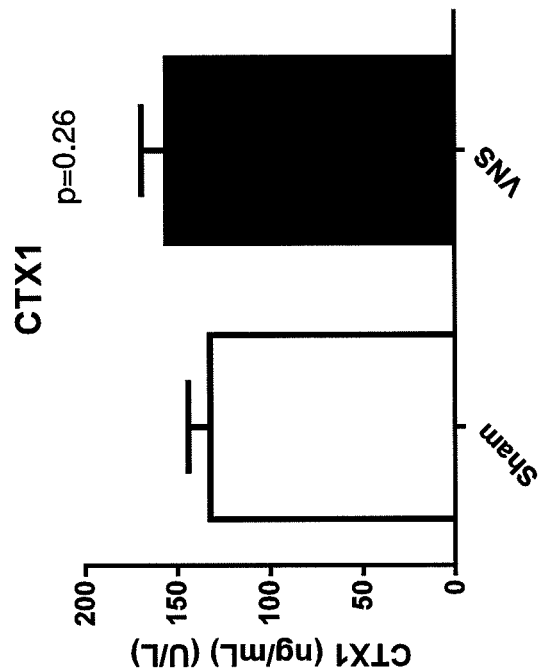
FIG. 14C shows a comparison between sham and VNS rats examining CTX1.
Figure 14B:
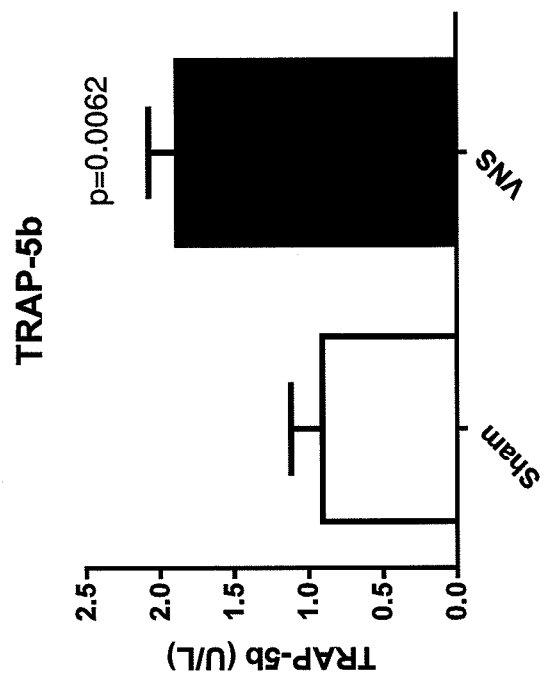

In FIG. 14A, the ratio of CTX1/TRAP-5b is consistent with the reduction in osteoclast activity seen in animals stimulated with VNS, compared to sham animals. FIGS. 14B and 14C illustrate the serum levels of TRAP-5b and CTX1, respectively. Serum levels of TRAP-5b is thought to be a metric for osteoclast number, but not activity. Similarly, the level of CTX1 was also examined at the same terminal blood draw, as shown in FIG. 14B. CTX1 is believed to be a measure of osteoclast activity/bone degradation. The reduction in total activity of the osteocytes is consistent with the morphological/histological data (showing less bone erosion) and with the RANL/OPG data. Although the precise mechanism of action of vagal stimulation in reducing resorption of bone by osteoclast, it is clear that VNS in the ranges descried herein significantly reduces the amount of bone erosion.

Figure 15A:
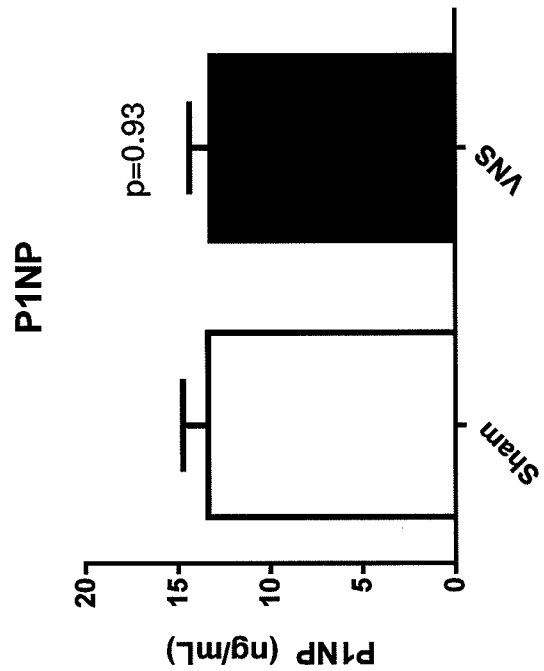
FIG. 15A compares sham and VNS-treated rats for levels of Osteocalcin, a marker of bone formation.
Figure 15B:
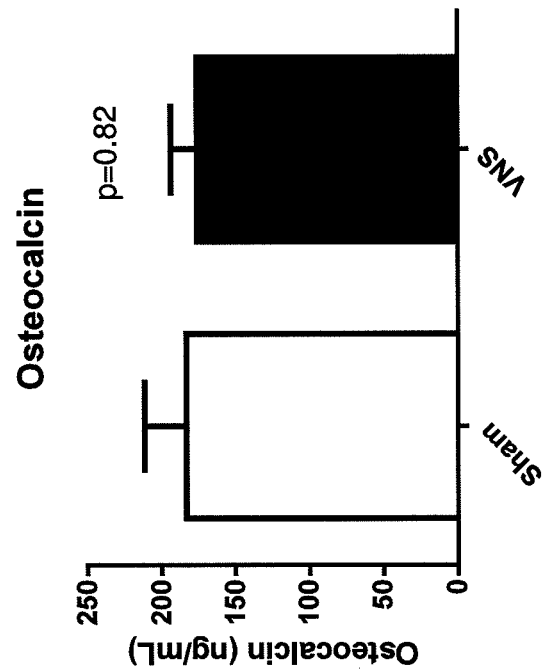
FIG. 15B shows a comparison between sham and VNS treated rats for levels of P1NP (procollagen type 1 N-terminal peptide), another marker of bone formation.

Further, stimulation of the vagus using the parameters described herein does not appear to significantly affect bone formation in the same animals. FIGS. 15A and 15B illustrate a lack of effect of VNS in the same animals examined in FIGS. 1-10B on bone formation. In FIG. 15A, the levels of Osteocalcin, a marker for bone formation, is not significantly different between sham and VNS animals. In FIG. 15B, P1NP (pro-collagen type 1 N-terminal peptide), a marker of one formation, if not significantly different between sham and VNS animals.

The examples provided herein are not intended to be comprehensive, but merely illustrate and embody certain variations of the invention. It is within the abilities of one of ordinary skill in the art to understand and apply, without undue experimentation, the invention as described herein.

What may be claimed is:

1. A method of treating a metastatic cancer or preventing a cancer from metastasizing, the method comprising applying electrical stimulation to the vagus nerve using a nerve stimulation device to reduce RANKL level within a patient having a metastatic cancer or at risk for developing a metastatic cancer from cancerous or precancerous cells or tissue.

2. The method of claim 1, wherein the step of applying electrical stimulation to the vagus nerve comprises repeatedly applying electrical stimulation of between about 0.1 and about 10 mA to the patient's vagus nerve for less than about 2 minutes, followed by an off-time of between about 12 and about 48 hours.

3. The method of claim 1, wherein the metastatic cancer is breast cancer, prostate cancer, myelomas, or bone cancers.

4. The method of claim 1, further comprising placing a nerve cuff around a portion of the subject's vagus nerve.

5. The method of claim 1, further comprising monitoring the patient's RANKL level.

6. The method of claim 1, further comprising monitoring a marker related to osteoclast number, activity or number and activity.

7. The method of claim 1, wherein applying stimulation to the vagus nerve to reduce RANKL level within a patent at risk for metastatic cancer comprises:
   stimulating the vagus nerve once a day; and reducing RANKL to between about 80-90%.

8. A method of treating a metastatic cancer or preventing a cancer from metastasizing, the method comprising:
   repeatedly applying electrical stimulation of between about 0.1 and about 10 mA to the patient's vagus nerve for less than about 2 minutes, followed by an off-time of between about 12 and about 48 hours, to reduce RANKL; and
   monitoring a marker related to RANKL, OPG or RANKL and OPG.

9. The method of claim 8, further comprising placing a nerve cuff around a portion of the subject's vagus nerve.

10. The method of claim 8, further comprising monitoring a marker related to the metastatic cancer.

11. The method of claim 8, further comprising monitoring a marker related to osteoclast number, activity or number and activity.

12. The method of claim 8, wherein repeatedly applying stimulation to the vagus nerve comprises: stimulating the vagus nerve once a day; and reducing RANKL to between about 80-90%.

\* \* \* \* \*